US008888730B2

(12) United States Patent
Rossi et al.

(10) Patent No.: US 8,888,730 B2
(45) Date of Patent: Nov. 18, 2014

(54) PERFUSION SYSTEM WITH RFID FEATURE ACTIVATION

(71) Applicant: Sorin Group Italia, S.r.l., Milan (IT)

(72) Inventors: Ivan Rossi, Poggio Rusco (IT); Raffaella Bombarda, Carpi (IT)

(73) Assignee: Sorin Group Italia S.r.l., Milan (IT)

( * ) Notice: Subject to any disclaimer, the term of this patent is extended or adjusted under 35 U.S.C. 154(b) by 0 days.

(21) Appl. No.: 13/622,634

(22) Filed: Sep. 19, 2012

(65) Prior Publication Data

US 2014/0079590 A1    Mar. 20, 2014

(51) Int. Cl.
| | |
|---|---|
| A61M 37/00 | (2006.01) |
| A61M 1/36 | (2006.01) |
| A61M 1/32 | (2006.01) |
| A61M 1/10 | (2006.01) |
| G06F 21/00 | (2013.01) |

(52) U.S. Cl.
CPC ............ *A61M 1/1086* (2013.01); *A61M 1/3666* (2013.01); *A61M 1/3613* (2014.02); *A61M 1/32* (2013.01); *A61M 1/10* (2013.01); *A61M 2205/6054* (2013.01); *A61M 2205/27* (2013.01); *A61M 2205/6018* (2013.01); *G06F 21/00* (2013.01)
USPC .......................... 604/6.14; 604/6.13; 604/4.01

(58) Field of Classification Search
USPC .................................. 604/4.01–6.16; 705/2, 3
See application file for complete search history.

(56) References Cited

U.S. PATENT DOCUMENTS

| | | | |
|---|---|---|---|
| 6,852,090 B2 | 2/2005 | Burbank et al. | |
| 7,435,200 B2 | 10/2008 | Kim et al. | |
| 7,435,220 B2 * | 10/2008 | Ranucci | 600/483 |
| 7,762,989 B2 | 7/2010 | Simpson | |
| 7,927,286 B2 | 4/2011 | Ranucci | |
| 7,931,601 B2 | 4/2011 | Ranucci | |
| 7,955,295 B2 * | 6/2011 | Lee et al. | 604/29 |
| 8,105,265 B2 * | 1/2012 | Demers et al. | 604/6.15 |
| 2002/0103453 A1 | 8/2002 | Burbank et al. | |
| 2004/0051368 A1 | 3/2004 | Caputo et al. | |
| 2009/0012449 A1 | 1/2009 | Lee et al. | |
| 2009/0088731 A1 * | 4/2009 | Campbell et al. | 604/890.1 |
| 2009/0099498 A1 | 4/2009 | Demers et al. | |
| 2009/0204075 A1 | 8/2009 | Simpson | |

(Continued)

FOREIGN PATENT DOCUMENTS

| | | |
|---|---|---|
| WO | WO02095675 A1 | 11/2002 |
| WO | WO03026724 A1 | 4/2003 |

(Continued)

OTHER PUBLICATIONS

European Search Report issued in EP Application No. 10160466, mailed Aug. 30, 2010, 3 pages.

(Continued)

*Primary Examiner* — Philip R Wiest
*Assistant Examiner* — Benjamin Klein
(74) *Attorney, Agent, or Firm* — Faegre Baker Daniels LLP

(57) ABSTRACT

The disclosure pertains to a perfusion system that is easy to set-up, use and monitor during a bypass procedure. In some embodiments, the disclosure pertains to a perfusion system in which at least some of the disposable components used with the perfusion system are configured to be able to communicate set-up and/or operational parameters to the perfusion system in order to unlock further functionality within the perfusion system.

15 Claims, 18 Drawing Sheets

(56) References Cited

U.S. PATENT DOCUMENTS

2011/0181394 A1 7/2011 Blair
2011/0230822 A1 9/2011 Lee et al.
2011/0257576 A1 10/2011 Simpson et al.

FOREIGN PATENT DOCUMENTS

WO   WO2006083933 A1   8/2006
WO   WO2007120812 A2   10/2007
WO   WO2011144747 A1   11/2011

OTHER PUBLICATIONS

European Search Report issued in EP Application No. 12187203, completed Nov. 1, 2013, 7 pages.
European Search Report issued in EP Application No. 12194981, completed Feb. 4, 2013, mailed Feb. 13, 2013.
International Search Report and Written Opinion issued in PCT/IB2011/051643, mailed Jul. 11, 2011, 9 pages.
International Search Report and Written Opinion issued in PCT/IB2013/056071, completed Nov. 1, 2013, mailed Nov. 8, 2013, 10 pages.

* cited by examiner

FIG. 23 though the blood. Concurrently, carbon dioxide is removed across the membrane. The oxygenated blood is then returned through an arterial line to the aorta, femoral, or other main artery.

PERFUSION SYSTEM WITH RFID FEATURE ACTIVATION

TECHNICAL FIELD

The disclosure pertains generally to perfusion systems and more particularly to integrated perfusion systems configured to communicate component-specific information between system components.

BACKGROUND

Perfusion entails encouraging physiological solutions such as blood through the vessels of the body or a portion of a body of a human or animal. Illustrative examples of situations that may employ perfusion include extracorporeal circulation during cardiopulmonary bypass surgery as well as other surgeries. In some instances, perfusion may be useful in providing extracorporeal circulation during various therapeutic treatments. Perfusion may be useful in maintaining the viability of body parts such as specific organs or limbs, either while the particular body part remains within the body, or while the body part is exterior to the body such as for transplantation or if the body part has been temporarily removed to provide access to other body structures. In some instances, perfusion may be used for a short period of time, typically defined as less than about six hours. In some cases, perfusion may be useful for extended periods of time that are greater than about six hours.

In some instances, blood perfusion systems include one or more pumps in an extracorporeal circuit that is interconnected with the vascular system of a patient. Cardiopulmonary bypass (CPB) surgery typically requires a perfusion system that allows for the temporary cessation of the heart by replacing the function of the heart and lungs. This creates a still operating field and allows for the surgical correction of vascular stenosis, valvular disorders, and congenital heart and great vessel defects. In perfusion systems used for cardiopulmonary bypass surgery, an extracorporeal blood circuit is established that includes at least one pump and an oxygenation device to replace the functions of the heart and lungs.

More specifically, in cardiopulmonary bypass procedures, oxygen-poor blood (i.e., venous blood) is gravity-drained or vacuum suctioned from a large vein entering the heart or other veins (e.g., femoral) in the body and is transferred through a venous line in the extracorporeal circuit. The venous blood is pumped to an oxygenator that provides for oxygen transfer to the blood. Oxygen may be introduced into the blood by transfer across a membrane or, less frequently, by bubbling oxygen through the blood. Concurrently, carbon dioxide is removed across the membrane. The oxygenated blood is then returned through an arterial line to the aorta, femoral, or other main artery.

SUMMARY

According to an embodiment of the present invention, an integrated perfusion system includes a heart lung machine having a plurality of pump modules, each pump module having a control unit. A controller is in communication with each of the control units. An input device is in communication with the controller and is configured to accept operational settings information from a user. An output device is in communication with the controller and is configured to display operational parameters of the plurality of pump modules. The integrated perfusion system includes a data management system that is in communication with the controller.

The data management system includes an RF sensor and a processor in communication with the RF sensor. One or more disposable elements are configured to be used in conjunction with the heart lung machine and include an RFID tag programmed with identifying information that can be read by the RF sensor and used by the processor to unlock functionality within the data management system.

According to another embodiment of the present invention, an integrated perfusion system includes a heart lung machine and a data management system, the data management system including an RF sensor. The integrated perfusion system may be configured by attaching a disposable component having an RFID tag to the heart lung machine, reading the RFID tag with the RF sensor, unlocking functionality within the data management system in accordance with information read from the RFID tag, and operating the unlocked functionality.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 23 is a schematic illustration of a screen capture in accordance with an embodiment of the invention.

DETAILED DESCRIPTION

The disclosure pertains to a perfusion system that is easy to set-up, use and monitor during a bypass procedure. In some embodiments, the disclosure pertains to a perfusion system in which at least some of the disposable components used with the perfusion system are encoded with set-up and/or operational parameters. In some embodiments, the disclosure pertains to a perfusion system in which at least some of the disposable components used with the perfusion system are encoded with identifying information that can unlock additional functionality within the perfusion system.

In some embodiments, the disclosure pertains to a blood level sensor that can be used to monitor a blood level or volume within a blood reservoir. The blood level sensor may be utilized in an integrated perfusion system in which the disposable components are configured, as noted above, to communicate with the perfusion system. In some embodiments, the blood level sensor may be utilized with a perfusion system lacking communication with disposables.

Figure 1:
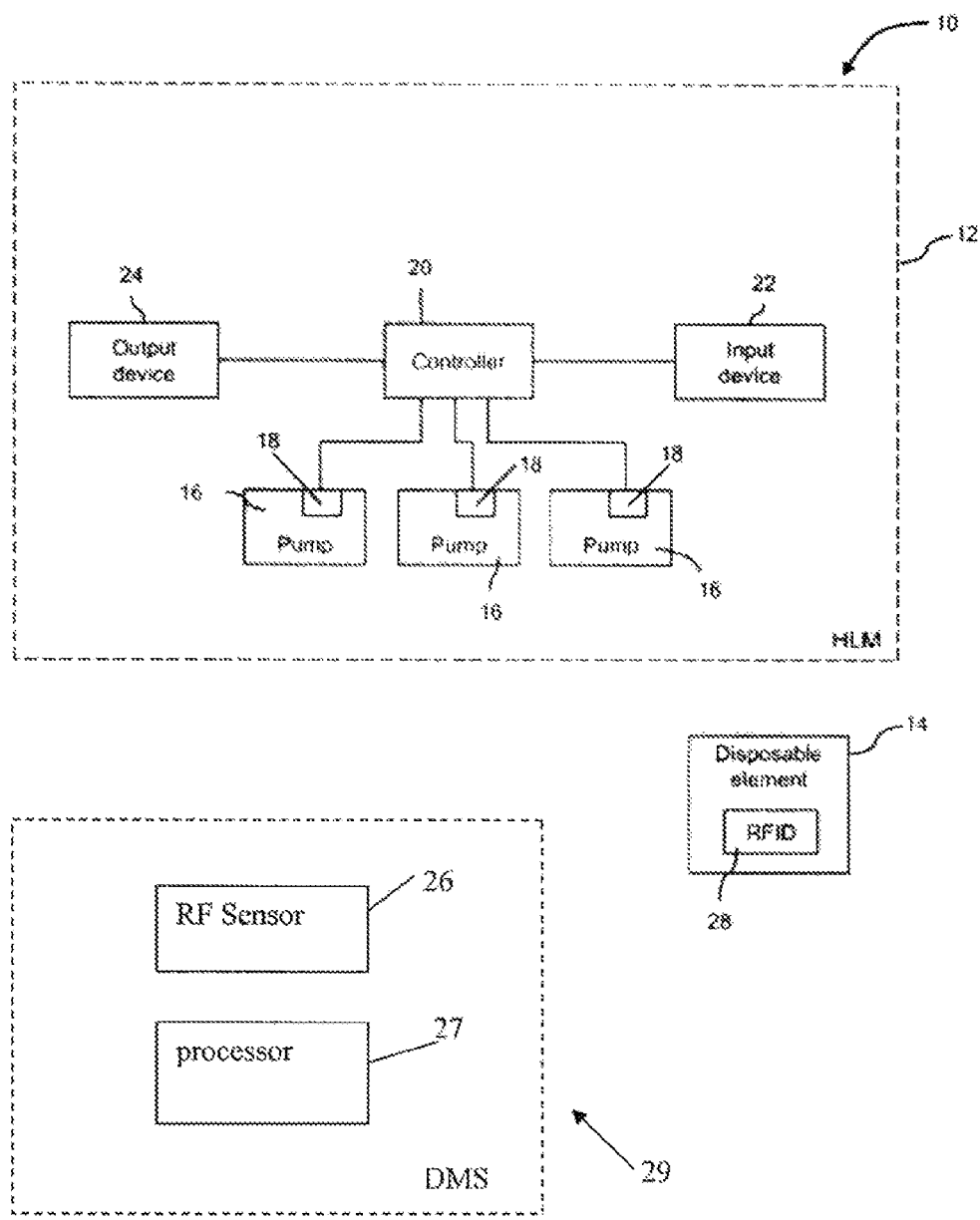
FIG. 1 is a schematic illustration of an integrated perfusion system including a heart lung machine and a data management system in accordance with an embodiment of the invention.

FIG. 1 is a schematic illustration of an integrated perfusion system 10. The integrated perfusion system 10 includes a heart lung machine (HLM) 12 and a disposable element 14. In some embodiments, as illustrated, the integrated perfusion system 10 also includes a data management system (DMS) 29. While the HLM 12 and the DMS 29 are illustrated as distinct components, it will be appreciated that in some embodiments, at least some of the functionality of the DMS 29 may be integrated into the HLM 12. In some embodiments, the HLM 12 and the DMS 29 are modular components or systems that can be connected together as desired, or used separately.

In some instances, at least some of the functionality described with respect to the DMS 29 may instead be incorporated into an inline blood monitor, or ILBM. An ILBM may be connected to the HLM 12 and may measure and/or monitor data directly via a sensor on a blood line. In some embodiments, an ILBM may receive information from the HLM 12 and/or the DMS 29. An ILBM may accept manually inputted data, and may display data that is manually inputted or received from the HLM 12 or other devices.

It will be appreciated that while only a single disposable element 14 is shown for ease of illustration, in many embodiments a plurality of different disposable elements 14 may be utilized in combination with the HLM 12. Each of the HLM 12, the disposable element 14 and the DMS 29 will be described in greater detail subsequently. The HLM 12 includes a number of different components. It is to be understood that the particular components illustrated herein as being part of the HLM 12 is merely an example, as the HLM 12 may include other components or different numbers of components.

In the illustrated embodiment, the HLM 12 includes three pump modules 16, but may include as few as two pump modules 16 or as many as six or seven pump modules 16. In some embodiments, the pump modules 16 may be roller or peristaltic pumps. In some embodiments, one or more of the pump modules 16 may be centrifugal pumps. Each of the pump modules 16 may be used to provide fluid for delivery to or removal from the heart chambers and/or surgical field. In an illustrative but non-limiting example, one pump module 16 draws blood from the heart, another provides surgical suction and a third provides cardioplegia fluid (high potassium solution to arrest the heart). Additional pump modules 16 (not shown) may be added to provide additional fluid transfer.

Each pump module 16 includes a control unit 18. In some embodiments, each control unit 18 may be configured to operate and monitor the operation of the particular pump module 16 to which it is attached or otherwise connected to. In some embodiments, each control unit 18 may include one or more input devices (not illustrated) such as switches, knobs, buttons, touch screens and the like so that the perfusionist may adjust the operation of the particular pump module 16. Each pump module 16 may include an alphanumeric display that the control unit 18 can use to display, for example, the value of a setting, the value of a current operating parameter, confirmation that the pump module 16 is operating normally, and the like.

The HLM 12 includes a controller 20 that is in communication with the control units 18 and that is configured to operate the HLM 12. In some embodiments, the controller 20 is configured to monitor one or more sensors that may be distributed on the HLM 12 and/or within the disposable element 14 to monitor operation of the HLM 12. Examples of such sensors (not illustrated for ease of illustration) include but are not limited to flow meters, pressure sensors, temperature sensors, blood gas analyzers and the like.

While the control units 18 and the controller 20 are illustrated as distinct elements, in some embodiments it is contemplated that these elements may be combined in a single controller. In some embodiments, it is contemplated that the control units 18, in combination, may be configured to operate the HLM 12, thereby negating a need for the controller 20.

The controller 20 communicates with an input device 22 and an output device 24. The input device 22 may be used by the perfusionist to enter information that is not otherwise entered into the control units 18. The output device 24 may be used by the HLM 12 to display pertinent information to the perfusionist. In some embodiments, the input device 22 may be a key pad, a keyboard, a touch screen, and the like. In some embodiments, the output device 24 may be a monitor. In some embodiments, either of the input device 22 and/or the output device 24 may be a computer such as a personal computer, a laptop computer, a notebook computer or a tablet computer. In some cases, the input device 22 and the output device 24 may be manifested in a single computer.

In some embodiments, the DMS 29 may be considered as functioning as a flight recorder, recording data from a variety of sources, including the HLM 12 and various external sensors and monitoring devices. In some instances, as illustrated, the DMS may include an RF sensor 26 and a processor 27. The DMS 29 may communicate with the HLM 12. In some embodiments, as described herein, the DMS 29 may also provide additional functionality that can be unlocked during use of the HLM 12 and/or the DMS 29.

The DMS 29 is configured to receive and record data from the HLM 12. In some embodiments, the DMS 29 may receive and record data from other sources as well, such as external devices. The DMS 29 may include an input device that permits a user to manually enter information. In some embodiments, as discussed herein, the DMS 29 may be configured to operate and display additional functionality. In some embodiments, the DMS 29 may be configured such that at least some of the disposable components 14 used with the integrated perfusion system 10 are encoded with identifying information that can unlock additional functionality within the DMS 29. A variety of different additional functionality may be unlocked, depending on the identity of the disposable component.

In some embodiments, the DMS 29 may be configured to operate and display a metabolic algorithm. An illustrative but non-limiting example of a suitable metabolic algorithm is known as the Ranucci algorithm. The Ranucci algorithm provides continuous and real-time information regarding the patient's oxygen delivery (DO2) and their carbon dioxide production values (VCO2), as well as the adequacy of the DO2 with respect to the patient's metabolic requirements. The Ranucci algorithm is described, for example, in U.S. Pat. Nos. 7,435,220; 7,927,286; and 7,931,601, which are incorporated by reference herein.

The RF sensor 26 may be configured to receive information from an active RFID tag placed on the disposable element 14, including the aforementioned identity of the disposable component.

In some embodiments, the RF sensor 26 may be a hand held device that is used to scan a passive RFID tag on the disposable element 14. According to other embodiments, the RF sensor 26 is replaced with any of a variety of known wireless communication receivers. The disposable element 14 includes an RFID tag 28. According to various embodiments, the disposable element 14 includes either an active RFID tag or a passive RFID tag (or both) configured to communicate with the RF sensor 26. In other embodiments, the RFID tag 28 is replaced with any of a variety of known wireless communication transmitters.

Passive RFID tags lack a power supply, and instead are powered by an induced current caused by an incoming radio-frequency scan. Because there is no onboard power supply, a passive RFID tag is smaller and less expensive. An active RFID tag includes an onboard power supply such as a battery. While this increases the size and expense of the RFID tag, an advantage is that the RFID tag can store more information and can transmit further. RFID tags, whether active or passive, may be selected to transmit at a variety of frequencies depending on need. Options include low frequency (about 100 to 500 kilohertz), high frequency (about 10 to 15 megahertz), ultra high frequency (about 860 to 960 megahertz) and microwave (about 2.45 gigahertz).

As noted above, the disposable element 14 may be considered as generically representing one, two or a plurality of different disposable elements that may be used in conjunction with the HLM 12. Illustrative but non-limiting examples of disposable elements 14 include tubing sets, blood reservoirs, oxygenators, heat exchangers and arterial filters. In some embodiments, a tubing set includes a number of different tubes, potentially of different lengths and sizes, for providing fluid flow between components of the HLM 12 as well as providing fluid flow between the HLM 12 and a patient.

In some embodiments, the disposable element 14 may be a blood reservoir such as a venous blood reservoir, a vent blood reservoir, a cardiotomy or suction blood reservoir. In some embodiments, the disposable element 14 may be a blood reservoir that combines one or more of a venous blood reservoir, a vent reservoir and/or a suction reservoir in a single structure. In some embodiments, one or more of the aforementioned sensors may be disposable elements that include an RFID tag 28 either to provide information identifying the sensor or even for transmitting sensed values to the controller 20.

The RFID tag 28 may be attached to the disposable element 14 in any appropriate manner. In some embodiments, the RFID tag 28 may be adhesively secured to the disposable element 14. In some embodiments, the RFID tag 28 may be molded into the disposable element 14. In some embodiments, the RFID tag 28 may be a stand alone card, similar in size and shape to a credit card, that may simply be packed with the disposable element 14 in such a way that it can be removed by the user and swiped by the RF sensor 26. However the RFID tag 28 is attached, the RFID tag 28 may be programmed with or otherwise configured to include a wide variety of information pertaining to the disposable element 14.

In some embodiments, the RFID tag 28 may include data or identifying information for the disposable element 14. Illustrative but non-limiting examples of identifying information include the name of the particular disposable element 14, a reference code, a serial number, a lot number, an expiration date and the like. In some embodiments, this information may be communicated to the controller 20 and may, for example, be used by the controller 20 to confirm that the proper disposable elements 14 are being used for a particular setting, patient or the like. As an example, the controller 20 may recognize that a pediatric tubing set is being used in combination with an adult-sized blood reservoir or other component. As another example, the controller 20 may recognize that an expected component is missing. There are a variety of other potential mismatches in equipment that may be recognized by the controller 20 as a result of the information provided by the RFID tag 28 attached to each of the one or more disposable elements 14.

In some embodiments, the RFID tag 28 may include descriptive or design information for the disposable element 14. Illustrative but non-limiting examples of descriptive or design information include specific materials, a list of components, priming volume of a component or tubing circuit, tubing size, tubing length, minimum and maximum working pressures, minimum and maximum working volume, and the like. In some embodiments, this information may be communicated to the controller 20 and may be used by the controller 20 to at least partially configure and/or operate the HLM 12. As an example, the controller 20 may use the sizing information provided from each of the disposable elements 14 to determine a working blood volume for the HLM 12.

In some embodiments, the information obtained from the RFID tag 28 may also be provided to the perfusionist. In some embodiments, the output device 24 may be configured to provide alphanumeric or graphical representations of the obtained information. In some cases, the RFID tag 28 may include instructional information that may be displayed by the output device 24 in order to instruct the perfusionist in optimal setup and/or operation of a particular disposable element 14. The RFID tab 28 may include warning information that can be transmitted from the RFID tag 28 and displayed on the output device 24. In some embodiments, this warning information may supplement or even replace warning information that might otherwise be included as printed materials packaged with the disposable elements 14.

In various embodiments, the output device 24 may be a computer such as a personal computer, a laptop computer, a notebook computer or a tablet computer. In some embodiments, the RFID tag 28 may include displayable information that, for example, suggests an optimal circuit design based upon the specific components being used, or perhaps updated use instructions. In some embodiments, information from the RFID tag 28 is displayed on the DMS 29.

In some embodiments, the RFID tag 28 may include information that a manufacturer of the disposable element 14 wants to provide to the user. Examples of such information may include technical features of the disposable element 14 that have changed from a previous version or even a previous batch. Another example includes information that can be displayed by the output device 24 that require the user to acknowledge receipt of the information before the controller 20 proceeds with a particular procedure. In some cases, the RFID tag 28 may receive error messages from the DMS 29 and/or the controller 20, and the RFID tag 28 may then be returned to the manufacturer, thereby providing the manufacturer with feedback regarding the performance of the disposable element 14 as well as other components.

In some embodiments, the RFID tag 28 may include information that can be used by an inventory tracking system. In some embodiments, the inventory tracking system may be in communication with the perfusion system 10. In some embodiments, the inventory tracking system may independently and directly receive information from the RFID tag 28 without communicating through the perfusion system 10.

Figure 2:
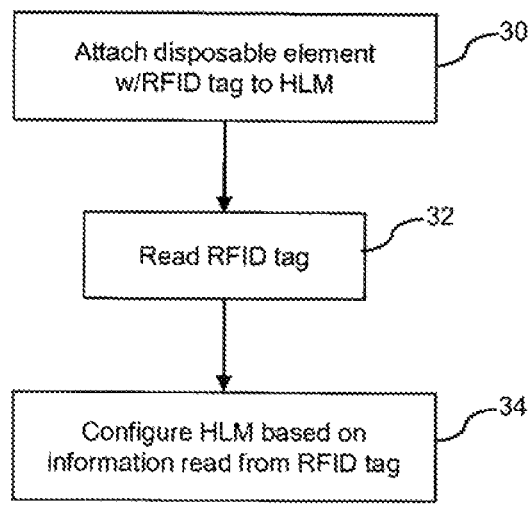
FIG. 2 is a flow diagram illustrating a method that can be carried out by the integrated perfusion system of FIG. 1.

FIG. 2 is a flow diagram illustrating a method that may be carried out using the perfusion system 10 of FIG. 1. A disposable element 14 having an RFID tag 28 may be attached to the HLM 12, as generally shown at block 30. At block 32, the RFID tag 28 is read. As noted above, the RFID tag 28 may be an active RFID tag or a passive RFID tag. In some embodiments, the RFID tag 28 may be read before the disposable element 14 is attached to the HLM 12. In some embodiments, the RFID tag 28 may be read after attachment. At block 34, the HLM 12 is configured based at least in part upon information that was read from the RFID tag 28 at block 32. In some embodiments, the controller 20 automatically configures the HLM 12 in response to this information. In some embodiments, at least some of the information read from the RFID tag 28 may be captured by the DMS 29.

Figure 3:
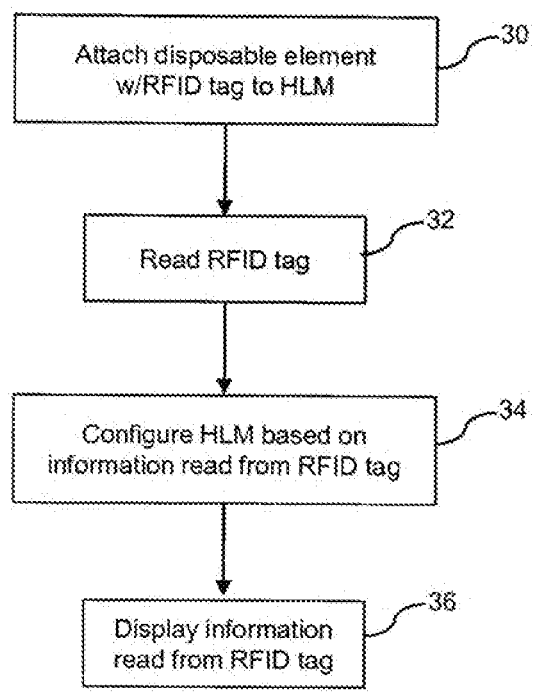
FIG. 3 is a flow diagram illustrating a method that can be carried out by the integrated perfusion system of FIG. 1.

FIG. 3 is a flow diagram illustrating a method that may be carried out using the perfusion system 10 of FIG. 1. A disposable element 14 having an RFID tag 28 may be attached to the HLM 12, as generally shown at block 30. At block 32, the RFID tag 28 is read. The RFID tag 28 may be read either before or after the disposable element 14 is attached to the HLM 12. At block 34, the HLM 12 is configured based at least in part upon information that was read from the RFID tag 28 at block 32. In some embodiments, the controller 20 automatically configures the HLM 12 in response to this information. At least some of the information read from the RFID tag 28 may be displayed on the output device 24, as seen at block 36, or on the DMS 29.

Figure 4:
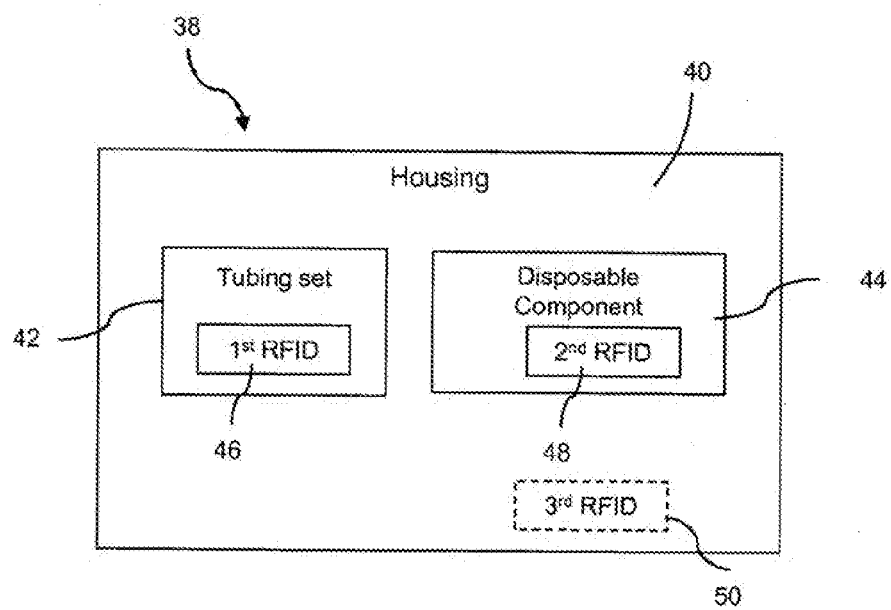
FIG. 4 is a schematic illustration of a heart lung machine pack that may be utilized with the integrated perfusion system of FIG. 1.

FIG. 4 is a schematic illustration of a heart lung machine pack 38 that may be utilized with the perfusion system 10 of FIG. 1. In some embodiments, the heart lung machine pack 38 may include all of the disposable elements 14 that will be used together for a particular patient and may be customized for the particular patient. In some embodiments, the heart lung machine pack 38 may include a housing 40 that, once filled, can be sealed up to keep the contents clean and sterile.

In the illustrated embodiment, the heart lung machine pack 38 includes a tubing set 42 and a disposable component 44. The tubing set 42 may include a plurality of different tubes. The disposable component 44 may be any of the disposable components discussed above with respect to the disposable element 14. In some embodiments, the heart lung machine pack 38 will include a plurality of different disposable components 44. The tubing set 42 includes a first RFID tag 46 while the disposable component 44 includes a second RFID tag 48. As discussed above, each of the first RFID tag 46 and the second RFID tag 48 may be either active or passive RFID tags and may include readable information pertaining to the component to which they are attached. In some instances, the housing 40 may include a third RFID tag 50 that, for example, identifies the contents of the heart lung machine pack 38. In some embodiments, the first RFID tag 46 and the second RFID tag 48 may not be included, as the third RFID tag 50 may be encoded with all of the information for the tubing set 42 and the disposable component 44.

Figure 5:
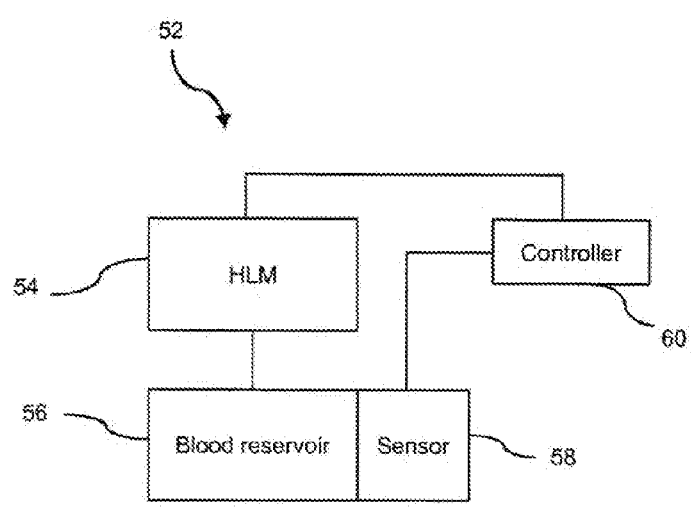
FIG. 5 is a schematic illustration of a perfusion system in accordance with an embodiment of the invention.

FIG. 5 is a schematic illustration of a perfusion system 52. The perfusion system 52 includes an HLM 54 that in some embodiments may be similar in structure and operation to the HLM 12 discussed with respect to FIG. 1. The perfusion system 52 also includes a blood reservoir 56, a blood level sensor 58 and a controller 60. The blood reservoir 56 may be a venous blood reservoir, a vent blood reservoir, a cardiotomy or suction blood reservoir. In some embodiments, the blood reservoir 56 may be a blood reservoir that combines one or more of a venous blood reservoir, a vent reservoir and/or a suction reservoir in a single structure.

The blood level sensor 58 may be configured to continuously monitor a variable blood level within the blood reservoir 56. The blood level sensor may be chosen from a variety of different sensing technologies. In some embodiments, as will be discussed subsequently with respect to FIGS. 12 and 13, the blood level sensor 58 may be an ultrasonic sensor in which ultrasound is used to detect the blood level within the blood reservoir 56. In some embodiments, the blood level sensor 58 may be an optical sensor in which a laser beam or light from an infrared light source is reflected by the liquid-air interface and the reflected light beam is detected by the blood level sensor 58. According to exemplary embodiments, the blood level sensor 58 is an optical distance sensor of the type commercially sold by Leuze electronic GmbH located in Owen/Teck, Germany (e.g., ODSL8, ODSL 30, or ODS 96). In some embodiments, the blood level sensor 58 may be a load cell or scale that is configured to measure a mass of the blood reservoir 56 and thereby determine the volume of blood therein.

In some embodiments, the blood level sensor 58 may be a capacitive sensor (better illustrated in subsequent Figures) that outputs an electrical signal that is proportional to or otherwise related to a blood level within the blood reservoir 56. The electrical signal may be communicated in either a wired or wireless fashion to the controller 60. While the controller 60 is shown as a distinct element, in some embodiments the controller 60 is manifested as part of a controller (similar to the controller 20) operating the HLM 54.

In some embodiments, the blood level sensor 58 may be modeled after capacitive sensors (e.g., CLC or CLW series) available commercially from Sensortechnics GmbH located in Puchheim, Germany, which are configured to provide contact-free measurement of continuous liquid level. The sensor available from Sensortechnics may be disposed on an outer surface of a container and provides an electrical signal representative of the liquid level within the container. In some instances, the Sensortechnics sensor may be spaced as much as about five millimeters from the liquid within the sensor, with no more than about twenty percent air gap between the sensor and the liquid. According to various embodiments, the capacitive sensor 58 is molded inside the blood reservoir 56, such that only the connector is accessible outside the reservoir. In these embodiments, the sensor 58 is protected by the plastic material of the blood reservoir.

In some embodiments, the sensor may undergo an initial configuration to adapt the sensor to the particulars of the container itself as well as the liquid within the container. In some embodiments, the blood level sensor 58 has a five pin electrical connection, including a voltage source, an analog signal out, a digital signal out, a teach-in pin and a ground. In some embodiments, the level sensor 58 is a capacitive sensor such as the Balluff SmartLevel sensor commercially sold by Balluff GmbH located in Neuhausen, Germany.

The controller 60 may receive an electrical signal that is proportional to or at least related to a blood level within the blood reservoir 56. The controller 60 may calculate a blood volume based on this electrical signal as well as a known shape or geometry of the blood reservoir 56. In some embodiments, the blood reservoir 56 may include an RFID tag (not illustrated) that provides the controller 60 with information pertaining to the known geometry of the blood reservoir 56.

If the blood reservoir 56 is a hard shell blood reservoir, the known geometry of the blood reservoir 56 may include the cross-sectional area of the blood reservoir 56, or a width and depth of the blood reservoir 56 as well as details on how this cross-sectional area varies relative to height within the blood reservoir 56. If the blood reservoir 56 is a soft shell reservoir, the known geometry may be based at least in part upon a known lateral expansion rate of the soft shell reservoir relative to the blood level within the blood reservoir 56.

Figure 6:
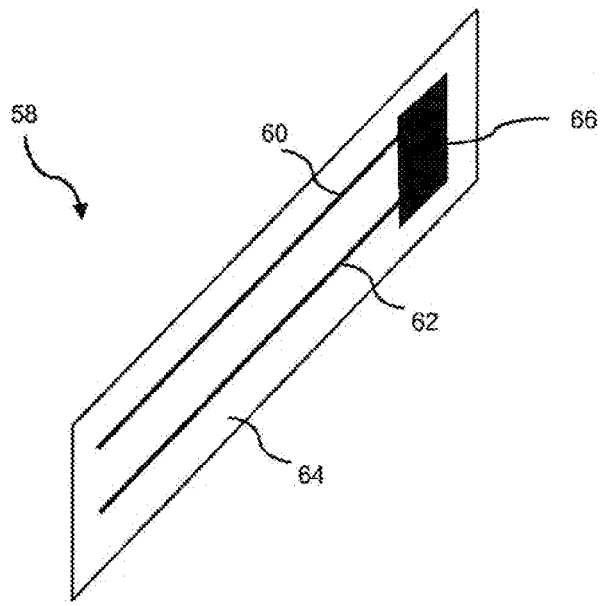
FIG. 6 is an illustration of a blood level sensor that may be utilized with the perfusion system of FIG. 5.

As can be seen in FIG. 6, the blood level sensor 58 includes a first elongate electrode 60 and a second elongate electrode 62. The first elongate electrode 60 and the second elongate electrode 62 are disposed along a flexible substrate 64. In some embodiments, the flexible substrate 64 may include an adhesive layer that can be used to secure the blood level sensor 58 to the blood reservoir 56. A connector socket 66 is secured to the flexible substrate 64 and is electrically connected to the first elongate electrode 60 and the second elongate electrode 62 in order to permit an electrical connection between the first and second electrodes 60, 62 and an electrical cable (not illustrated in this Figure). In some embodiments, rather than an elongate sensor, the blood level sensor 58 may include two or more distinct SMARTLEVEL™ capacitive sensors such as those available commercially from Balluff. These sensors may provide a binary, yes/no signal. By locating several of these sensors at differing levels proximate the blood reservoir 56, the blood level within the blood reservoir 56 may be determined.

Figure 7:
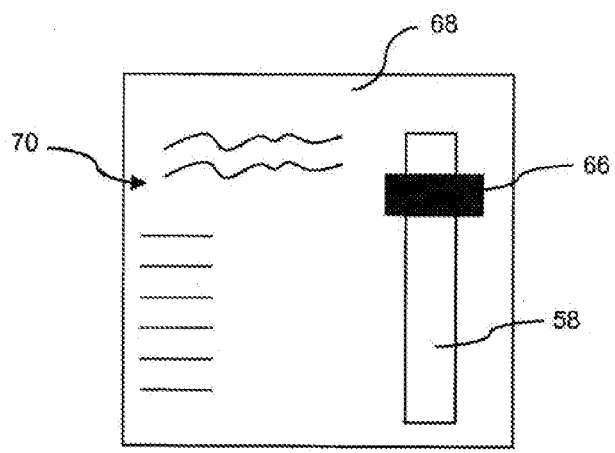
FIG. 7 is an illustration of a blood level sensor incorporated into a label that may be utilized with the perfusion system of FIG. 5.

In some embodiments, the blood level sensor 58 may be attached to or otherwise integrated into a label 68 as seen in FIG. 7. The label 68 may include various indicia 70 such as use instructions, volume indicators and the like. In some embodiments, the label 68 may include an adhesive side for attachment to an outer surface of the blood reservoir 56. In some embodiments, the label 68 is oriented on the blood reservoir such that a lower portion of the blood level sensor 58 is aligned at or near a bottom of the blood reservoir 56.

Figure 12:
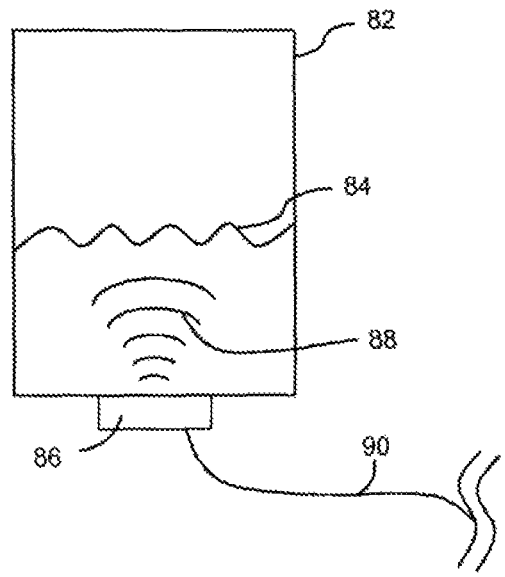
FIG. 12 is an illustration of a blood reservoir including a blood level sensor in accordance with an embodiment of the invention.
Figure 13:
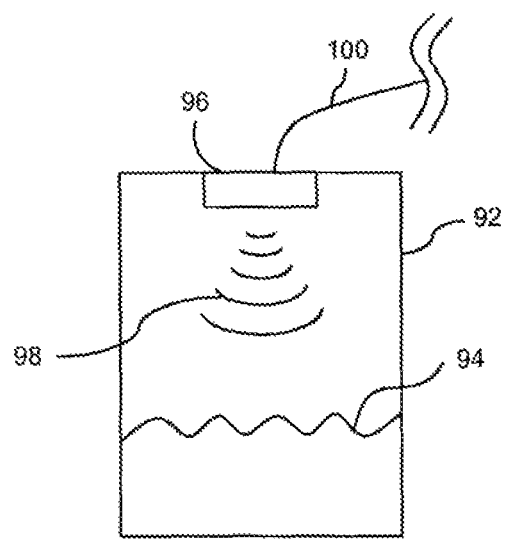
FIG. 13 is an illustration of a blood reservoir including a blood level sensor in accordance with an embodiment of the invention.

In some embodiments, the blood level sensor may be an ultrasonic blood level sensor, as illustrated in FIGS. 12 and 13. FIG. 12 is an illustration of a blood reservoir 82 that contains a volume of blood. The volume of blood defines an interface 84 between the volume of blood and the air or other fluid within the blood reservoir 82. In some embodiments, an ultrasonic transducer 86 that is located at or near a lower surface of the blood reservoir 82 can be used to locate the interface 84 by transmitting ultrasonic waves 88 towards the interface 84. The reflectance of the ultrasonic waves 88 depend at least in part upon the fluid they are passing through. Thus, by measuring the reflectance, the ultrasonic transducer 86 can determine how far away the interface 84 is and thereby determine the fluid level. Based on the fluid level and the geometric configuration of the blood reservoir 82, a controller may determine the blood volume within the blood reservoir 82. In some embodiments, a cable 90 transmits a signal from the ultrasonic transducer 86 to the controller. In some embodiments, the information is transmitted wirelessly, such as via an RFID tag attached to the ultrasonic transducer.

FIG. 13 is similar to FIG. 12, but shows a blood reservoir 92 having a blood volume defining an interface 94. In this embodiment, an ultrasonic transducer 96 is located at or near a top of the blood reservoir 92 and transmits ultrasonic waves 98 downward towards the interface 94. In some embodiments, a cable 100 transmits a signal from the ultrasonic transducer 96 while in other embodiments this is done wirelessly, such as with an RFID tag attached to the ultrasonic transducer 96. A primary difference between the embodiments shown in FIGS. 12 and 13 is that in FIG. 12, the interface 84 is detected from below, or through the blood, while in FIG. 13 the interface 94 is detected from above, or through the air.

In some embodiments, the blood level sensor may be an infrared (IR) light blood level sensor. In some embodiments, an infrared light source positioned at or near a lower surface of the blood reservoir 82 may be used to locate a fluid/air interface within the blood reservoir 82 by transmitting infrared light towards the interface. Alternatively, the infrared light blood level sensor may be located above the interface. In some embodiments, the infrared light blood level sensor may be located a short distance away from the blood reservoir 82 and thus can be attached to a mechanical holder for the blood level reservoir 82.

In some instances, the infrared light is reflected back towards the infrared light blood level sensor. By measuring the reflectance, the location of the interface may be determined. In some embodiments, the infrared light travels through the blood to an infrared light sensor located opposite the infrared light blood level sensor. By detecting changes in the received light, the interface location may be determined. By combining the interface location with known geometric parameters of the blood reservoir 82, the controller 20 can determine the blood volume within the blood reservoir 82. In some embodiments, this information is transmitted wirelessly to the controller 20, such as via an RFID tag attached to the infrared light blood level sensor.

Figure 8:
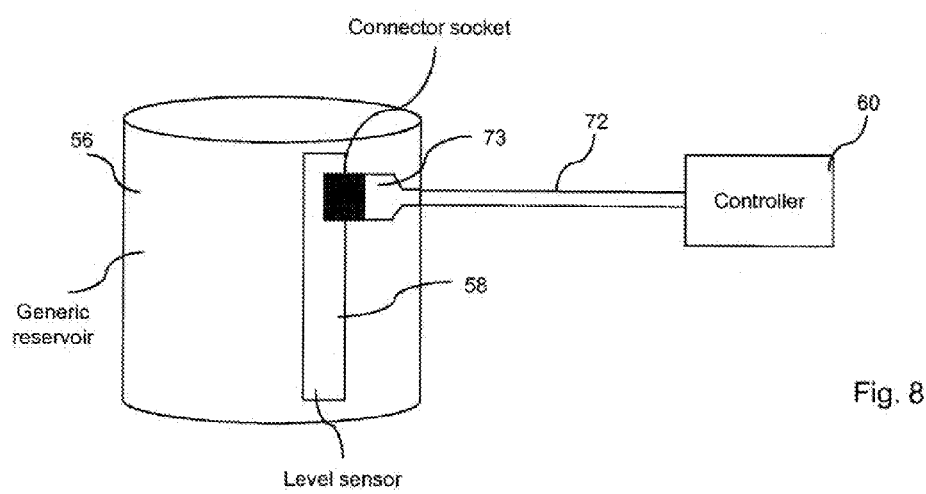
FIG. 8 is an illustration of a blood reservoir including a blood level sensor in accordance with an embodiment of the invention.

FIG. 8 is an illustration of the blood level sensor 58 attached to the blood reservoir 56. An electrical cable 72 provides an electrical connection between the blood level sensor 58 and the controller 60. The electrical cable 72 includes a plug 73 that is configured to connect to the electrical connector 66. In some embodiments, the plug 73 includes circuitry that converts a detected capacitance into a voltage signal that the controller 60 can use to calculate the blood volume. In some embodiments, the plug 73 further includes circuitry to calculate the blood volume.

Figure 9:
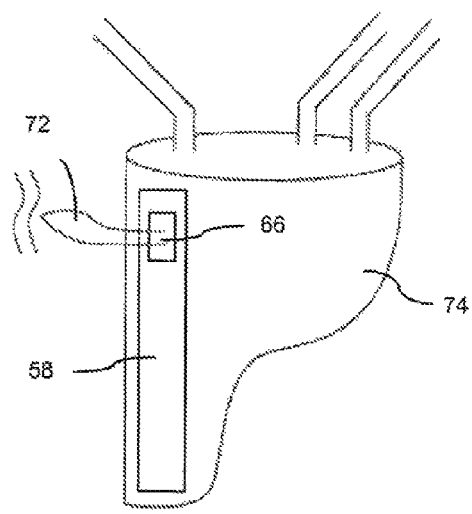
FIG. 9 is an illustration of a hard shell blood reservoir including a blood level sensor in accordance with an embodiment of the invention.
Figure 10:
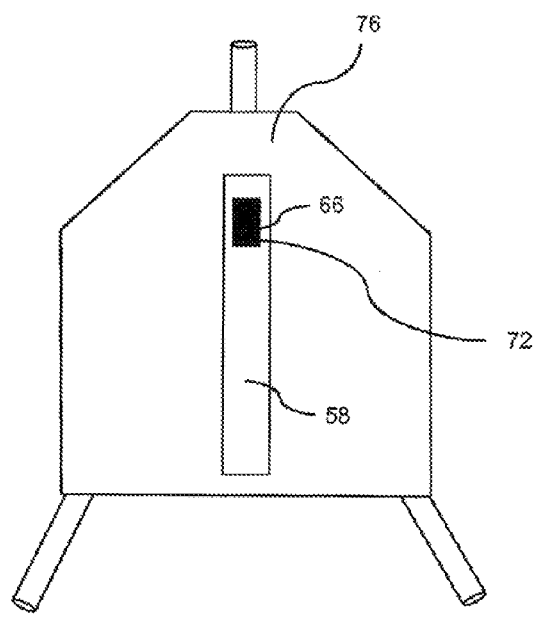
FIG. 10 is an illustration of a soft shell blood reservoir including a blood level sensor in accordance with an embodiment of the invention.

As noted above, the blood reservoir 56 may be either a hard shell reservoir or a soft shell reservoir. FIG. 9 illustrates a hard shell reservoir 74 bearing the blood level sensor 58 while FIG. 10 illustrates a soft shell reservoir 76 including the blood level sensor 58. In either case, the reservoir may be constructed to include the blood level sensor 58. In some embodiments, the blood level sensor 58 may be adhesively secured to an existing blood reservoir.

Figure 11:
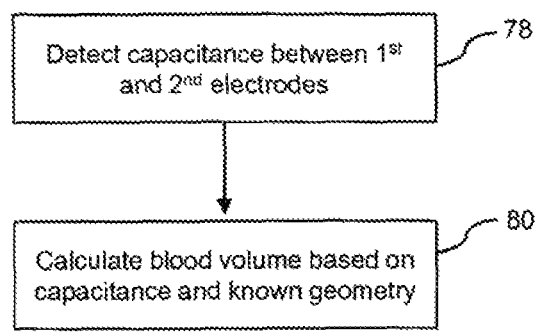
FIG. 11 is a flow diagram illustrating a method that can be carried out using the perfusion system of FIG. 5.

FIG. 11 is a flow diagram illustrating a method that may be carried out using the perfusion system 52 of FIG. 5. A capacitance between first and second electrodes may be detected, as referenced at block 78. In some embodiments, as discussed above, the capacitance may be converted into an electrical signal representing the blood level by circuitry within the plug 73. In embodiments using the CLC series Sensortechnics sensor, for example, the sensor will output a voltage between 0.5 and 4.5 volts. Assuming the sensor pad is appropriately located on the reservoir, this voltage indicates a level or height of the liquid in the reservoir. At block 80, the controller 60 may calculate a blood volume that is based upon the detected capacitance and a known dimensions or geometry of the blood reservoir 56. In some embodiments, the controller 60 (or other circuitry within the HLM 54) may provide the circuitry in the plug 73 with sufficient information (e.g., dimensions or geometry) regarding the blood reservoir 56 to permit the circuitry to perform the blood volume calculation. In some embodiments, the calculated blood volume is communicated to the HLM 54 so that it may adjust an operating parameter of the HLM 54. In various exemplary embodiments, the HLM 54 may alter a pump speed to either increase or decrease blood flow into or out of the blood reservoir 56. It may be important, for example, to prevent the blood level in the reservoir 56 from moving below a certain minimum level or volume. Accordingly, in various embodiments, the HLM 54 will compare the blood level or volume to this minimum level and adjust pump speed appropriately.

According to other embodiments, the HLM 54 may use the blood volume information for a variety of applications, including for example auto-regulation of pump occlusion, auto-loading of pump segments, conducting automatic occlusivity testing, performing automatic priming, automatic recirculating and debubbling, conducting automatic pressure tests, or performing automatic system emptying.

In some embodiments, and as noted above, the perfusion system 10 may be configured such that at least some of the disposable components used with the perfusion system 10 are encoded with identifying information that can unlock additional functionality within the perfusion system. A variety of different additional functionality may be unlocked, depending on the identity of the disposable component.

In some embodiments, for example, if the disposable component is or otherwise includes a tubing set (such as the tubing set 42 shown in FIG. 4), the tubing set may include an RFID tag (such as the 1$^{st}$ RFID 46 shown in FIG. 4) that is programmed or otherwise includes information that can be used by the perfusion system 10 to determine the priming volume of a blood circulation system. The blood circulation system may include only items included in the tubing set, or the blood circulation system may include additional items.

The presence of the tubing set may enable the DMS 29 to operate and display a priming volume simulator. In some embodiments, for example if a different tubing set is used, or perhaps a tubing set from a different manufacturer, the priming volume simulator may be disabled or otherwise not permitted to function. Hence, the presence of the particular tubing set (or other disposable component) may unlock the additional functionality of a priming volume simulator.

In some embodiments, the DMS 29 may be configured to operate and display an algorithm that monitors and/or provides data related to a patient's metabolism. In some embodiments, the algorithm may be unlocked by the DMS 29, depending on the identity of the disposable component 14. While a variety of different algorithms are known and may be unlocked by the DMS 29, an illustrative but non-limiting example of an algorithm that can be programmed into the perfusion system 10 and that may be unlocked if appropriate disposable components 14 are used includes a priming volume simulator. Another example is a metabolic algorithm is known as the Ranucci algorithm, referenced above.

In understanding and describing the Ranucci algorithm, certain definitions are useful.
HCT: hematocrit (%).
Hb: hemoglobin (g/dL).
CPB: cardiopulmonary bypass.
T: temperature (° C.).
VO2=oxygen consumption (mL/min).
VO2i=oxygen consumption indexed (mL/min/m$^2$).
DO2=oxygen delivery (mL/min).
DO2i=oxygen delivery indexed (mL/min/m$^2$).
O2 ER=oxygen extraction rate N.
VCO2=carbon dioxide production (mL/min).
VCO2i=carbon dioxide production indexed (mL/min/m$^2$).
Ve=ventilation (L/min).
eCO2=exhaled carbon dioxide (mmHg).
AT=anaerobic threshold.
LAC=lactates.
Qc=cardiac output (mL/min).
IC=cardiac index (Qc/m$^2$), (mL/min/m$^2$).
Qp=pump flow (mL/min).
IP=pump flow indexed (Qp/m$^2$), (mL/min/m$^2$).
CaO2=arterial oxygen content (mL/dL).
CvO2=venous oxygen content (mL/dL).
PaO2=arterial oxygen tension (mmHg).
PvO2=venous oxygen tension (mmHg).
a=arterial.
v=venous.
Sat=Hb saturation (%).

The following equations are useful in the Ranucci algorithm.

$$VO2=Qc\times(CaO2-CvO2) \text{ in a normal circulation} \quad (1)$$

$$VO2=Qp\times(CaO2-CvO2) \text{ during CPB} \quad (2)$$

$$DO2=Qc\times CaO2 \text{ in a normal circulation} \quad (3)$$

$$DO2=Qp\times CaO2 \text{ during CPB} \quad (4)$$

$$O2ER=VO2/DO2(\%) \quad (5)$$

$$Hb=HCT/3 \quad (6)$$

$$CaO2=Hb\times1.36\times Sat(a)+PaO2\times0.003 \quad (7)$$

$$CvO2=Hb\times1.36\times Sat(v)+PvO2\times0.003 \quad (8)$$

$$VCO2=Ve\times eCO2\times1.15 \quad (9)$$

The oxygen consumption (VO2) is the sum of the metabolic needs of each specific organ and thus represents the metabolic needs of the whole organism. Under basal conditions (at rest), it is about 3-4 mL/min/kg, i.e. about 250 ml/min for a subject weighting 70 kgs. Applying equations (3) and (7), the oxygen delivery (DO2) may be calculated, and is about 1000 mL/min. Therefore, a considerable functional reserve exists, since the DO2 is about 4 times greater than the VO2. The VO2 may increase depending on the metabolic needs (basically under physical exercise, but even in pathologic conditions like septic shock). A top level endurance athlete may reach a maximal VO2 of about 5000 mL/min.

Of course, to meet these increasing oxygen demands, the DO2 must increase as well: it can reach, in an athlete during exercise, the value of 6000 mL/min (Qc: 30 L/min with an unchanged arterial oxygen content of 20 mL/dL). As a consequence, the O2 ER may increase up to 75%.

Figure 14:
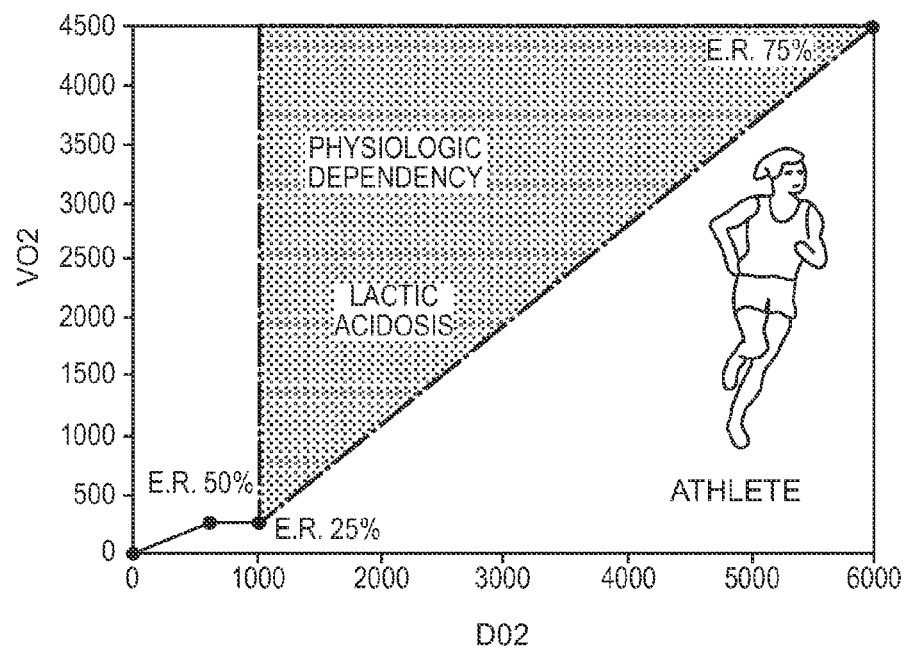
FIG. 14 is a graph illustrating the relationship between VO2 and DO2 in an athlete under physical exercise.

FIG. 14 is a diagram showing the relationship between DO2 and VO2 in an athlete during physical exercise. If the athlete (that, for example, is running a marathon) falls into the dark triangular zone (where the DO2 is unable to support the VO2), the athlete is forced to use other metabolic mechanisms in order to develop mechanical energy. In particular, the athlete will undergo anaerobic lactacid metabolism, which develops energy but at the expenses of lactic acid formation, local and systemic acidosis, and finally exercise stops usually within 2 minutes. In other words, the VO2 is physiologically dependent on the DO2.

In the medical field, of course, the situation is different. The DO2 may pathologically decrease in case of: decreased arterial oxygen content due to anemia; decreased arterial oxygen content due to hypoxia; and decreased cardiac output. However, due to the existence of the above-mentioned physiological reserve, the VO2 may be maintained even for a DO2 decrease down to about 600 mL/min (DO2i 320 mL/min/m$^2$), due to the increased O2 ER.

Figure 15:
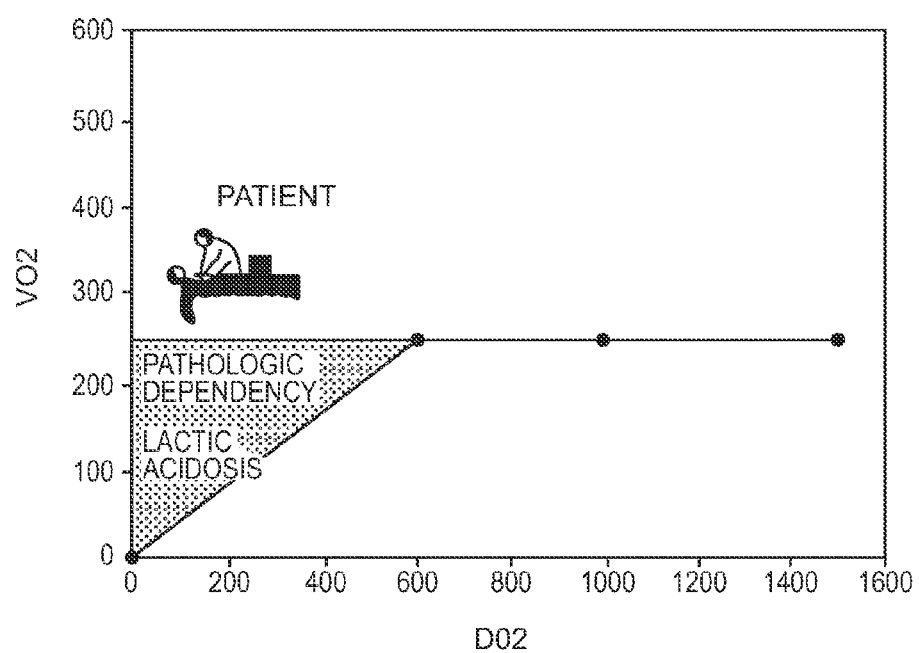
FIG. 15 is a graph illustrating the relationship between VO2 and DO2 in a patient under cardiac operation.

FIG. 15 is a diagram showing the relationship between DO2 and VO2 in the range observed during medical conditions (i.e. cardiac operation). Below a DO2 of 600 mL/min, VO2 starts decreasing. The patient meets, exactly as the athlete, a lactic acidosis, with lactate (LAC) production. In other words, the patient experiences a shock. The DO2 level below which the VO2 starts decreasing and becomes pathologically dependent on the DO2 is called the critical DO2 ($DO2_{crit}$). Maintaining the DO2 above this threshold is very important in many pathological conditions, to avoid an acidosis-shock status. The $DO2_{crit}$ is higher during a septic shock.

Since 1994, in a paper published in Perfusion, Ranucci and coworkers demonstrated that in a series of 300 consecutive patients that underwent myocardial revascularization with CPB, the presence of a severe hemodilution was an independent risk factor for a postoperative acute renal failure (ARF). In particular, the cut-off value was identified at an HCT<25%.

Subsequently, other authors have demonstrated that the lowest HCT during CPB was an independent risk factor for many "adverse outcomes" in cardiac surgery. Stafford-Smith and coworkers, in 1998 (Anesth Analg), confirmed the relationship between hemodilution and ARF.

More recently, the lowest hematocrit on CPB has been recognized as an independent risk factor for postoperative low cardiac output and hospital mortality by Fang and coworkers (Circulation, 1997), and for an impressive series of postoperative adverse events by Habib and coworkers in 2003 (J Thorac Cardiovasc Surg). The relationship between hemodilution and ARF has been subsequently confirmed by Swaminathan and coworkers in 2003 (Ann Thorac Surg), Ranucci and coworkers 2004 and 2005 (Ann Thorac Surg) and Karkouti and coworkers in 2005 (J Thorac Cardiovasc Surg). The critical HCT value below which the ARF risk significantly increases is located between 23% and 26%.

Almost all the authors ascribe this relationship to an insufficient oxygen supply (DO2) to the various organs. The kidney, in particular, due to its physiologic condition of hypoxic perfusion, seems to be at high risk.

Surprisingly, all the studies demonstrating a relationship between HCT and ARF or other organ damages failed to consider that the HCT is only one of the two determinants of the DO2 during CPB: the other is the pump flow (Qp). This would not influence the DO2 if the Qp was a constant, but this is not the case. In all the studies, the pump flow (Qp) varied from a Qpi of 2.0 L/min/m$^2$ to a Qpi of 3.0 L/min/m$^2$, and the variation was dependent on the perfusion pressure. An HCT of 24% results in a DO2i of 230 ml/min/m$^2$ if the Qpi is 2.0 L/min/m$^2$, and of 344 ml/min/m$^2$ if the Qpi is 3.0 L/min/m$^2$.

In a scientific paper in The Annals of Thoracic Surgery, Ranucci and coworkers actually demonstrated that the DO2i, rather than the HCT, is the best predictor of ARF. Moreover, in presence of perioperative blood transfusions, the DO2i remains the only determinant of ARF. The $DO2_{crit}$ identified in this paper is 272 ml/min/m$^2$, very close to the one previously defined as the DO2i below which the VO2 becomes pathologically dependent on the DO2. In other words, maintaining the DO2i above this threshold allows a decrease in the hypoxic organ dysfunction or the elimination of the hypoxic organ dysfunction; in presence of a low HCT, an adequate increase of the Qp may minimize the deleterious effects of hypoxemia. As a consequence, a continuous monitoring of the DO2 is of paramount importance in order to limit the postoperative complications, namely the renal ones.

Measuring a low HCT has poor clinical value, since the only possible (and arguable) countermeasure is a blood transfusion. On the other hand, the DO2 may be modulated by increasing the pump flow.

The level of $DO2_{crit}$, below which the LAC production begins, is identified by the concept of "anaerobic threshold" (AT). In athletes, it is the level of expressed mechanical power at which the LAC production begins; in a patient, it is the level of $DO2_{crit}$, below which the LAC production begins.

It has been demonstrated that the LAC value during CPB is predictive for postoperative complications. The problem is that the LAC value is not available on-line, and only some devices (blood gas analyzers) provide it. It is however possible to make an "indirect" assessment of the AT. As a matter of fact, under steady conditions, the VO2/VCO2 ratio is a constant, while during anaerobic lactacid metabolism the VCO2 increases more than the VO2. This happens because the lactic acid undergoes the following transformation: H LAC+NaHCO$_3$=LAC Na+H$_2$CO$_3$ and the H$_2$CO$_3$ is split into H$_2$O and CO$_2$, with a further CO$_2$ production.

Figure 16:
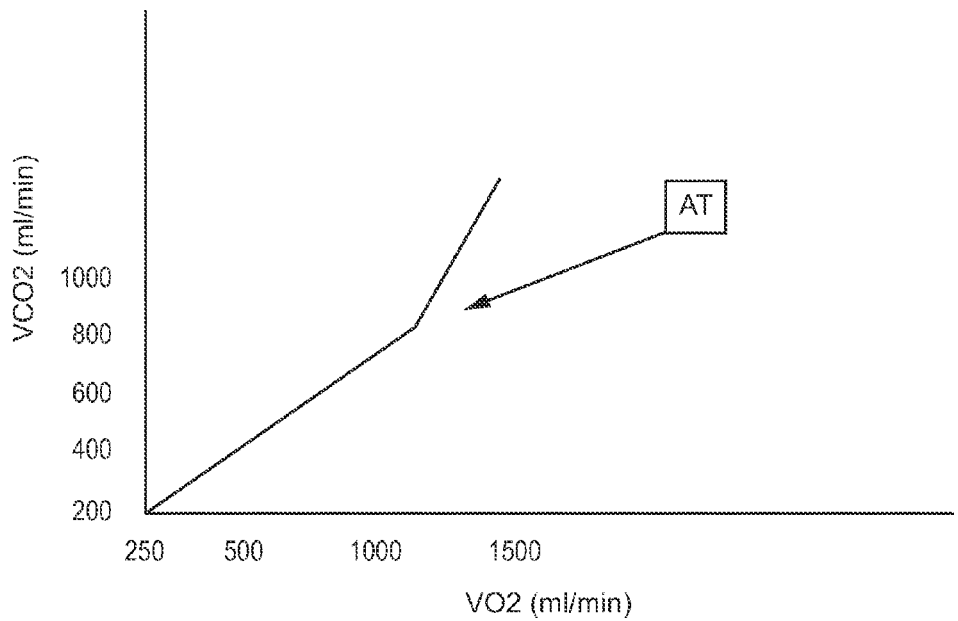
FIG. 16 is a graph illustrating the relationship between VCO2 and VO2.
Figure 17:
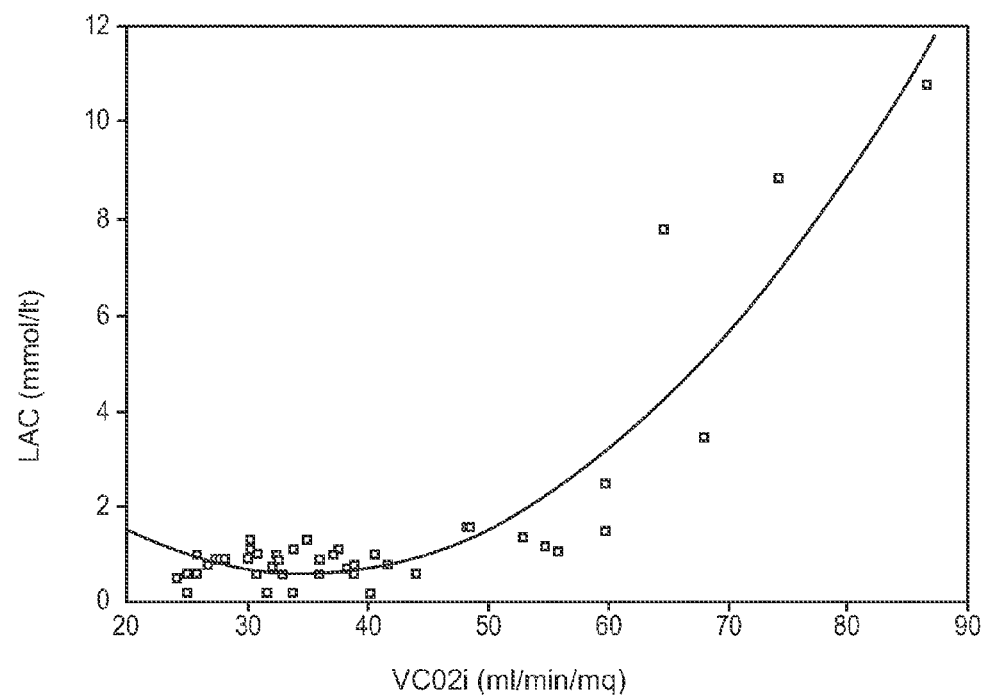
FIG. 17 is a graph illustrating the relationship between LAC and VCO2i.

FIG. 16 is a diagram showing the relationship between VO2 and VCO2. The relationship between VCO2 and LAC production has been demonstrated in 15 consecutive patients under CPB, in an experimental trial performed by the inventor himself. In FIG. 17, the graphical relationship between VCO2 and LAC production is reported. From this relationship, it appears that a VCOi value of 60 ml/min/m$^2$ is a sensitive predictor of lactic acidosis.

Under normal resting conditions, oxygen delivery matches the overall metabolic demands of the organs and the oxygen consumption (VO2) is about 25% of the oxygen delivery (DO2), and energy is produced basically through the aerobic mechanism (oxidative phosphorylation). When the DO2 starts decreasing (due to a decreased cardiac output, extreme hemodilution, or both), the VO2 is maintained until a "critical level" is reached. Below this critical point the oxygen consumption starts decreasing, becoming dependent on the oxygen delivery, and the failing aerobic energy production is progressively replaced by anaerobic adenosine triphosphate production (pyruvate conversion to lactate).

As a result, blood lactate concentration starts rising, and numerous studies have established the use of lactates as a marker of global tissue hypoxia in circulatory shock. Under these circumstances, the anaerobic metabolism results in an excess of proton production and tissue acidosis; buffering of the protons by bicarbonate ions results, in turn, in an anaerobic carbon dioxide production (VCO2). Therefore, below the critical DO2, there is a linear decrease of both VO2 and VCO2, but due to the anaerobic CO2 production, the respiratory quotient (VCO2/VO2) RQ increases. When the critical DO2 is reached due to a decrease in cardiac output (cardiogenic shock), the above relationship becomes more complex.

Due to the reduced pulmonary flow and to ventilation-perfusion mismatch, the ability of the lung to eliminate carbon dioxide is impaired, and carbon dioxide elimination and end-tidal carbon dioxide tension are decreased. Consequently, carbon dioxide starts accumulating in the venous compartment, and the venoarterial carbon dioxide gradient is increased. In other terms, the VCO2 (intended as carbon dioxide production by the tissues) becomes progressively higher than carbon dioxide elimination.

Under CPB conditions, the above pattern changes again. The artificial lung is much more efficient than the natural lung in terms of carbon dioxide clearance, and is maintained even for a very low pump flow. Not by chance, under specific circumstances like deep hypothermia and according to the pH strategy, it is clinically needed to add carbon dioxide to the gas flow in order to avoid dramatic and dangerous patterns of hypocapnia. In this setting, the VCO2 is strictly correlated to the carbon dioxide elimination.

Therefore, while in a normal setting the venous carbon dioxide tension (PvCO2) is inverse to the carbon dioxide elimination, during CPB the two parameters are positively correlated. Subsequently, Ranucci and coworkers found that the best predictor of hyperlactatemia during CPB was the DO2/VCO2 ratio, with a cut off value around 5.0, and the VCO2, with a cut off value at 60 mL/min/m2.

In some embodiments, it is believed that low values of DO2 during CPB may create an ischemic environment to the kidney. Extremely low values of DO2 may trigger anaerobic metabolism with lactate production. This may be detected using CO2-derived parameters In some embodiments, therefore, the integrated perfusion system 14 may include one or more of a pump flow reading device and a hematocrit value reading device. The integrated perfusion 10 system includes an input device 22 and a controller 20 that is programmed or otherwise configured to compute the oxygen delivery (DO2i) value on the basis of the measured pump flow (Qp), the measured hematocrit (HCT), the preset value of arterial oxygen saturation (Sat(a)), and the preset value of arterial oxygen tension (PaO2) and a display.

In some embodiments, the perfusion system 14 also includes a CO2 reading device for continuously detecting exhaled CO2 (eCO2) at the oxygenator gas escape of the HLM. The input device 22 allows the operator to insert a gas flow value (Ve) and the controller 20 computes the CO2 production (VCO2i) on the basis of the preset gas flow (Ve) value and the detected exhaled CO2 (eCO2), and the output device 24 shows the calculated value of CO2 production (VCO2i).

In some embodiments, the controller 20 is programmed or otherwise configured to compare the above mentioned oxygen delivery (DO2i) value with a threshold value of oxygen delivery (DO2i$_{crit}$) and to trigger an alarm when the oxygen delivery (DO2i) value falls below the threshold value of oxygen delivery (DO2i$_{crit}$). In one embodiment, the threshold value of oxygen delivery (DO2i$_{crit}$) is preset by the operator at a value of about 270 ml/min/m².

In some embodiments, the perfusion system 10 further includes a temperature detecting device configured to continuously measure a body temperature (T) of the patient and to send the temperature values to the controller 20, to be subsequently displayed by the output device 24. The controller 20 may be programmed or otherwise configured to calculate, based on the temperature (T) of the patient, an oxygen delivery threshold. In some embodiments, the controller 20 is programmed or otherwise configured to calculate the hemoglobin (Hb) value from the detected hematocrit (HCT) value.

Figure 18:
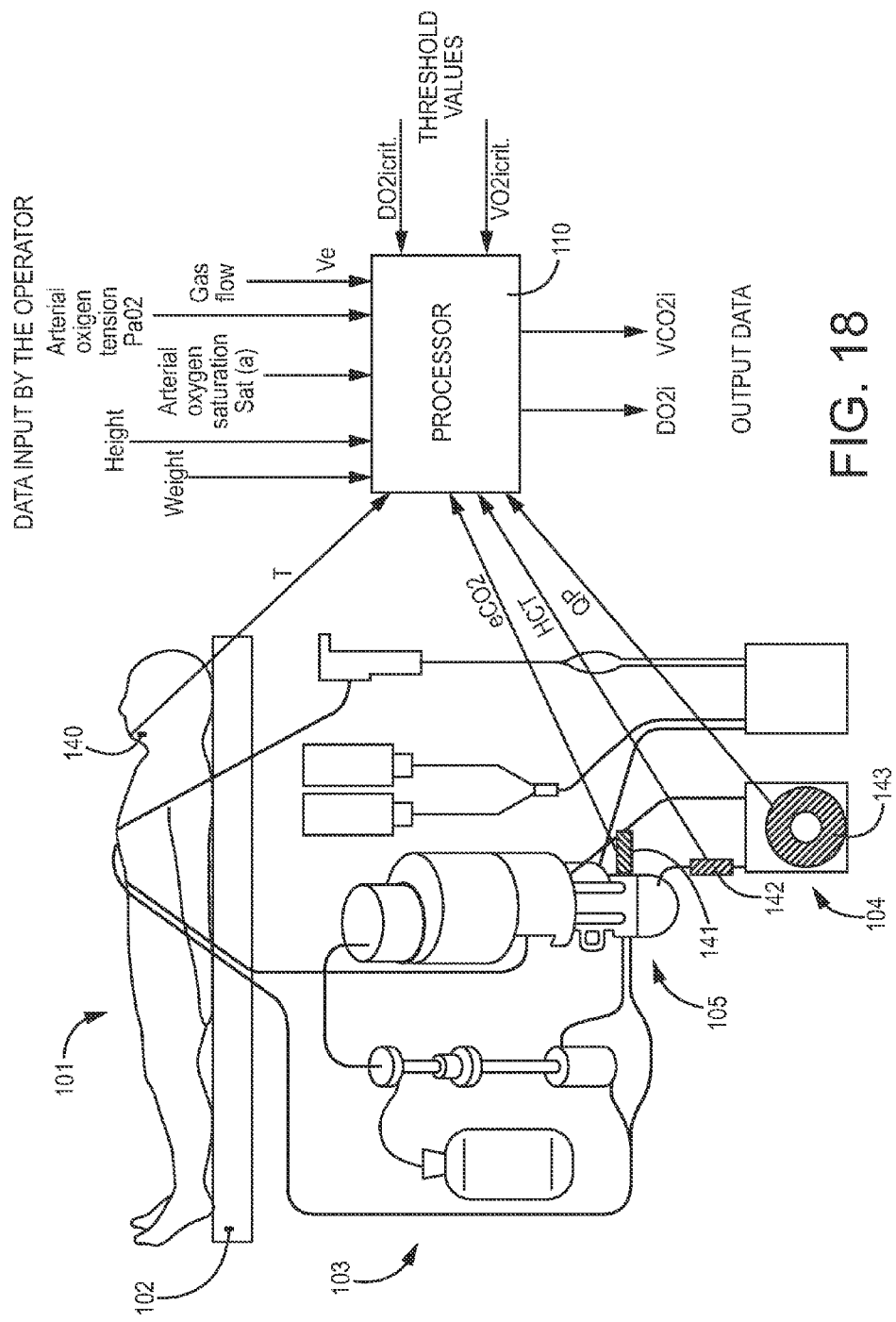
FIG. 18 is a schematic illustration of an embodiment of a perfusion system in accordance with an embodiment of the invention.

FIG. 18 shows a patient 101 laying on a surgical table 102. An embodiment of a HLM 103, is connected to the patient 101. A HLM 103 includes a venous extracorporeal circuit, collecting blood from the venous system of the patient. A roller or centrifugal mechanical pump 104 pumps the venous blood from a venous extracorporeal circuit towards an oxygenator 105, whose role is removing CO2 from the venous blood and supplying oxygen (O2). The blood oxygenated by the oxygenator 105, is sent, again by the same roller or centrifugal pump 104, to an arterial extracorporeal circuit connected to the arterial system of the patient, therefore creating a total bypass of the heart and lungs of the patient.

The monitoring system 110, is operatively connected to the heart-lung machine 103 and may include a processor that is able to perform calculations, as subsequently explained, and a monitor screen or display 111 that provides an interface with the operator. Using a knob 50 (seen in FIGS. 20 and 21), an operator may manually input data.

Examples of data that may be manually inputted include, but are not limited to, the height and weight of the patient and the arterial oxygen saturation (Sat(a)). While this value is usually 100 percent, in some situations such as oxygenator malfunction, the value may decrease. In some embodiments, the arterial oxygen saturation value may be continuously or discretely (every twenty minutes or so) monitored by an external device that may be connected to the DMS 29. In some embodiments, if the Sat(a) value is not monitored, the DMS 29 may be programmed to assume that it is 100%.

The arterial oxygen tension value (PaO2) may also be manually entered. The PaO2 value is measured by the perfusionist on the arterial blood of the patient with blood gas analysis, using an adequate and specific device. In some embodiments, the arterial oxygen tension value may be continuously or discretely (every twenty minutes or so) monitored by an external device connected to the DMS 29.

The gas flow value (Ve) may be manually entered. The Ve value is established by the perfusionist operating the heart-lung machine 103. Generally, the Ve is regulated with a flowmeter, according to the patient's parameters. This Ve value rarely changes during a CPB procedure, and therefore can be manually inserted by the operator. However, as an alternative, the monitoring system 110 may include an electronic flowmeter connected to the heart-lung machine 103, to continuously detect the Ve value.

In some embodiments, the DMS 29 may be configured to calculate and display the oxygen consumption rate (VO2) and/or the carbon dioxide production (VCO2). As noted above, the VO2 value may be calculated using equation 2 and the VCO2 value may be calculated using equation 9:

$$VO2 = Qp \times (CaO2 - CvO2) \text{ during CPB} \quad (2)$$

$$VCO2 = Ve \times eCO2 \times 1.15 \quad (9).$$

In some embodiments, the Ve value (gas flow) may be automatically and continuously acquired from a gas blender that is connected to the HLM 12. In some instances, the Ve value may be manually entered into the DMS 29. In some embodiments, the expired CO2 value (eCO2) may be continuously or discretely (about every twenty minutes or so) monitored by an external device connected to the HLM 12. The eCO2 value may be separately monitored and manually entered into the DMS 29.

In some embodiments, the monitoring device 110 is electrically connected to the HLM 103, so as to continuously receive data collected by adequate sensors placed in specific positions of the heart-lung machine. Illustrative but non-limiting examples of continuously collected data include the patient's body temperature (T). The temperature T may be continuously measured by a temperature probe 140 inserted inside the esophagus or the rectum or other organs of the patient. The temperature probe 140 sends an electronic signal of the temperature to a monitor of the HLM 103 visualizing, in real-time, the temperature value. In this case, it is sufficient to interface with an electrical connection the monitor of the HLM 103 with the monitoring device 110, for a continuous input of the temperature value T.

Another monitored value includes the exhaled carbon dioxide (eCO2). The eCO2 value is continuously measured through a CO2 detector 141 placed at the gas escape of the oxygenator 105 to detect the sidestream CO2 exhaled from the oxygenator 105. The CO2 detector 141 can be any kind of CO2 detector among the various commercially available and re-usable capnographs.

Another monitored value includes the hematocrit (HCT). The HCT value is continuously measured through a hematocrit reading cell 142 placed inside the arterial or venous circuit of the HLM 103. In some embodiments, the HCT value may be discretely measured, for example, about every twenty minutes or so by an external device that may be connected to the DMS 29. In some embodiments, the HCT value may be independently monitored and manually inputted into the controller 20 and/or the DMS 29. For instance, in FIG. 18, the hematocrit reading cell 142 is placed inside the arterial line between the pump 104 and the oxygenator 105. The hematocrit reading cell 142 is commercially available and disposable.

Another monitored value includes the pump flow rate (Qp). The Qp value is continuously measured through the Doppler reading cell 143, placed on the arterial line of the HLM 103. This kind of Doppler reading cell 143 measures the blood flow on the basis of the Doppler principle (red cells velocity).

In some embodiments, if the pump 104 is a centrifugal pump, it is already equipped with a Doppler reading cell 143. Conversely, if the pump 104 is a roller pump, the Doppler reading cell 143 may be added. In the alternative, the Doppler reading cell 143 may be omitted, since the roller pump head is provided with a flow measuring system. In this case, the data regarding the pump flow Qp is directly sent to the monitoring device 110.

With specific reference to FIG. 19, operation of the monitoring system 110 is described below. The processor of the monitoring system 110 includes a first computing program 112 that, based on the weight and height of the patient as input by the operator calculates, according to pre-defined tables, the body surface area (BSA) of the patient.

The BSA value is sent to a second computing program 113 that receives the input value of the pump flow Qp as detected by the pump 104 of the HLM 103. The second computing program 113 calculates the indexed pump flow Qpi, according to the relationship QpI=Qp/BSA.

A third computing program 114 receives the input value HCT as detected by the hematocrit reading cell 143 placed inside the venous or arterial line of the heart-lung machine. The third computing program 114, based on the equation (6), calculates the hemoglobin value Hb. The Hb value is sent to the display 111 and is displayed in a window 151 of the display 111 (FIG. 20).

The pump flow indexed Qpi computed by the second computing program 113 and the hemoglobin value Hb computed by the third computing program 114 are sent to a fourth computing program 115 that receives as input values the values of arterial oxygen saturation (Sat(a)) and arterial oxygen tension (PaO2) manually entered by the operator. The fourth computing program 115, according to the equation (4), calculates the indexed oxygen delivery value (DO2i).

Figure 20:
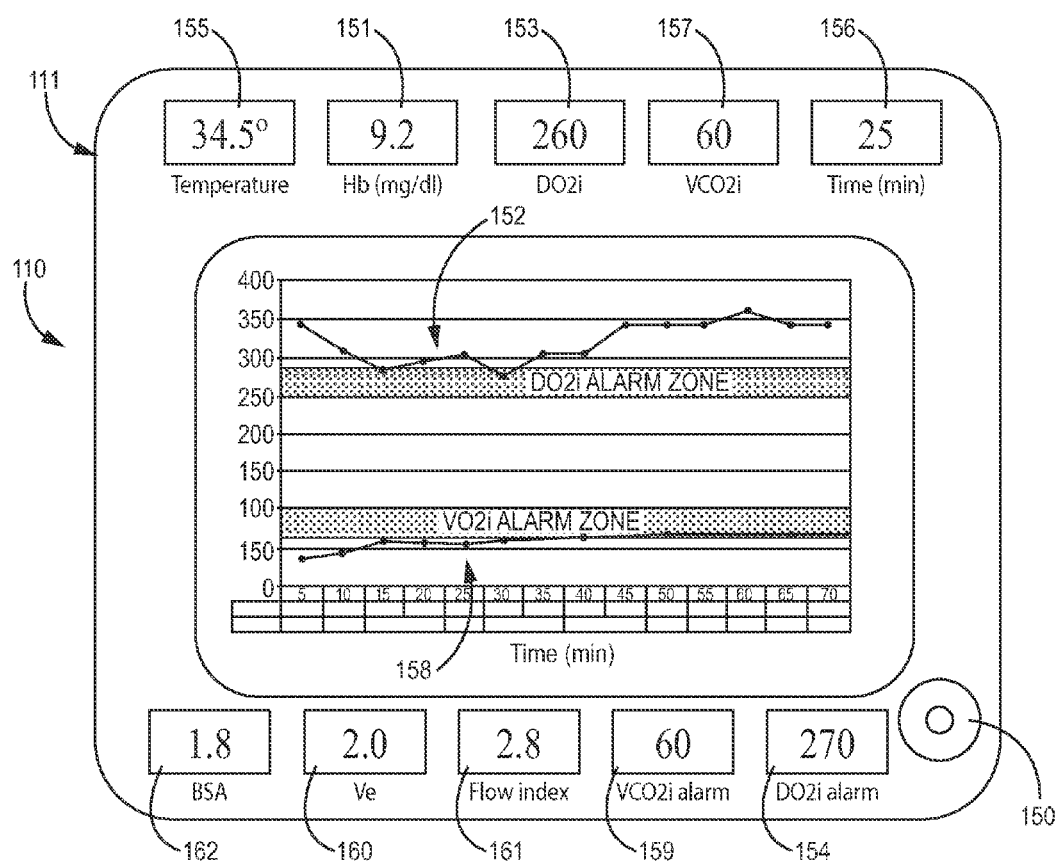
FIG. 20 is a schematic illustration of a screen capture in accordance with an embodiment of the invention.

As shown in FIG. 20, the DO2i value is visualized in real time in a window 153 of the display 111 and as a graphical pattern 152 (as a function of time). The display 111 is provided with a chronometer window 156 showing the time passed from the beginning of the CPB.

Figure 19:
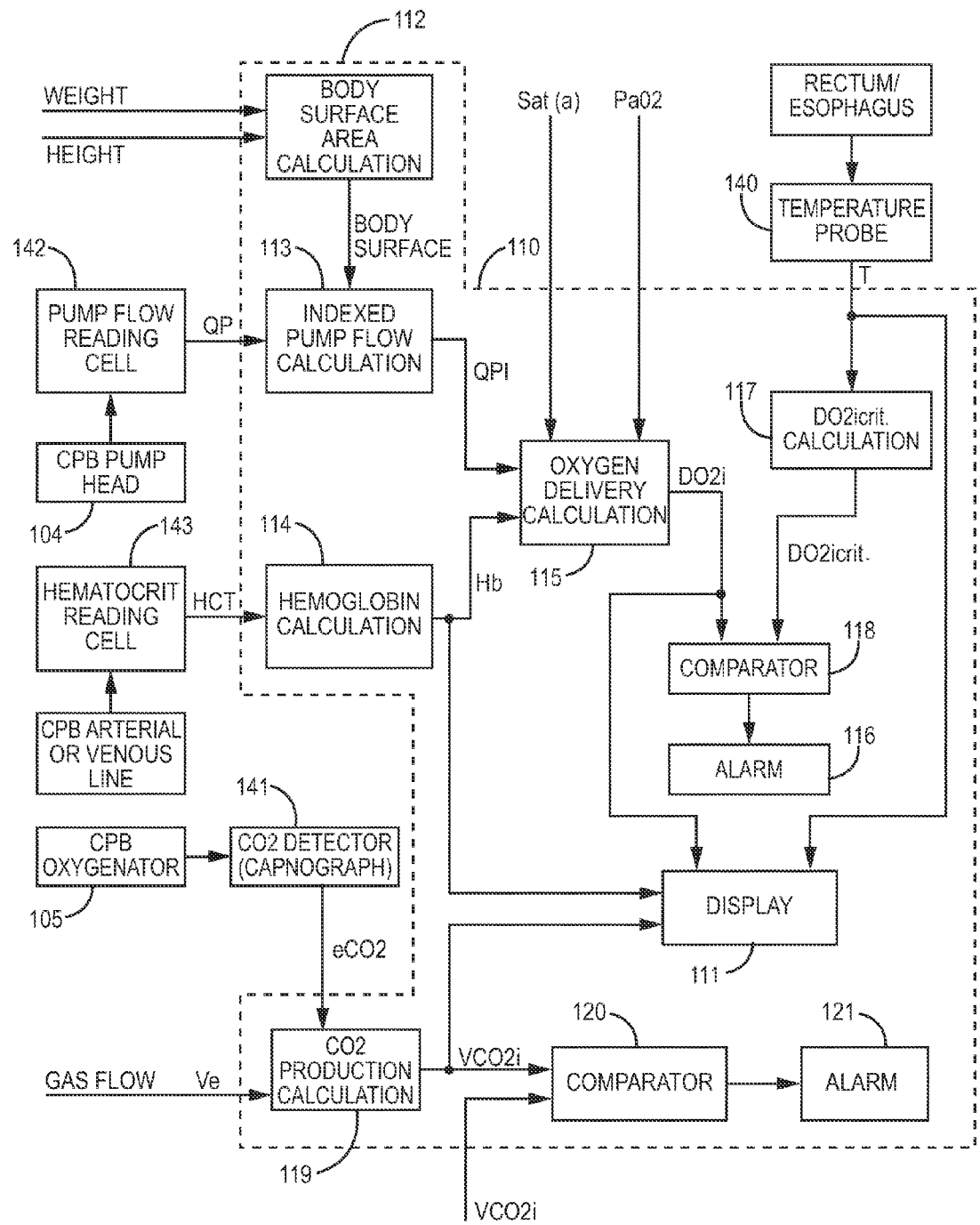
FIG. 19 is a block diagram illustrating a monitoring system in accordance with an embodiment of the invention.

As shown in FIG. 19, the DO2i value is sent to a comparator 118 which compares it to a threshold value of $DO2i_{crit}$ that is displayed in a window 154 (FIG. 20) of the display 111. This threshold value may be set at 270 ml/min/m$^2$ at a temperature between 34° C. and 37° C., and decreases as a function of temperature, in a linear fashion.

Therefore the threshold value of $DO2i_{crit}$ be preset by the operator or may be calculated by a computing program 117 depending on the temperature value T determined by the temperature probe 140. The temperature T value determined by the probe 140 is sent to the display 111 to be displayed in a window 155.

When the DO2i value falls below the $DO2i_{crit}$, the comparing device sends a control signal to an alarm 116 that is triggered, alerting the operator of a potentially dangerous condition.

In some embodiments, the alarm 116 is not triggered by brief decreases of the pump flow Qp (often needed during CPB). Therefore, the alarm 116 could be set to be activated after 5 minutes of consecutive detection of a DO2i below the DO2i. However, a recording of all the periods of low flow can be made, to analyze and avoid the possibility that many short periods of low flow may create an additional effect. It is reasonable to consider no more than 20 minutes (as a total) of DO2i below the $DO2i_{crit}$ during a normal CPB lasting about 90 minutes. The monitoring device 110 is equipped with a computing program 119, which receives as input values the exhaled carbon dioxide eCO2 as detected by the CO2 sensor 141 and the gas flow Ve set by the operator. According to these input data, the computing program 119 calculates the indexed carbon dioxide production VCO2i applying the equation (9).

The VCO2i value as calculated by the computing program 119 is sent to the display 111 and displayed in real time in a window 157 (FIG. 20) in its graphical relationship 158 as a function of time.

The VCO2i value is sent to a second comparator 120 which compares it with an anaerobic threshold value $VCO2i_{crit}$ set by the operator; by default the $VCO2i_{crit}$ is preset at 60 ml/min/m$^2$. As shown in FIG. 20, the display 111 is provided with a window 159 showing the value of anaerobic threshold $VCO2i_{crit}$ set by the operator.

Back to FIG. 19, when the VCO2i exceeds the $VCO2i_{crit}$ an alarm signal is sent to a second alarm 121, which, when triggered, alerts the operator of a warning condition. Moreover, as shown in FIG. 20, the display 111 is provided with: a window 160 where the gas flow value Ve set by the operator is displayed; a window 161 where the indexed pump flow value Qpi arriving from the computing program 113 is displayed; and a window 162 where the body surface area of the patient is displayed as calculated by the computing program 112.

Figure 21:
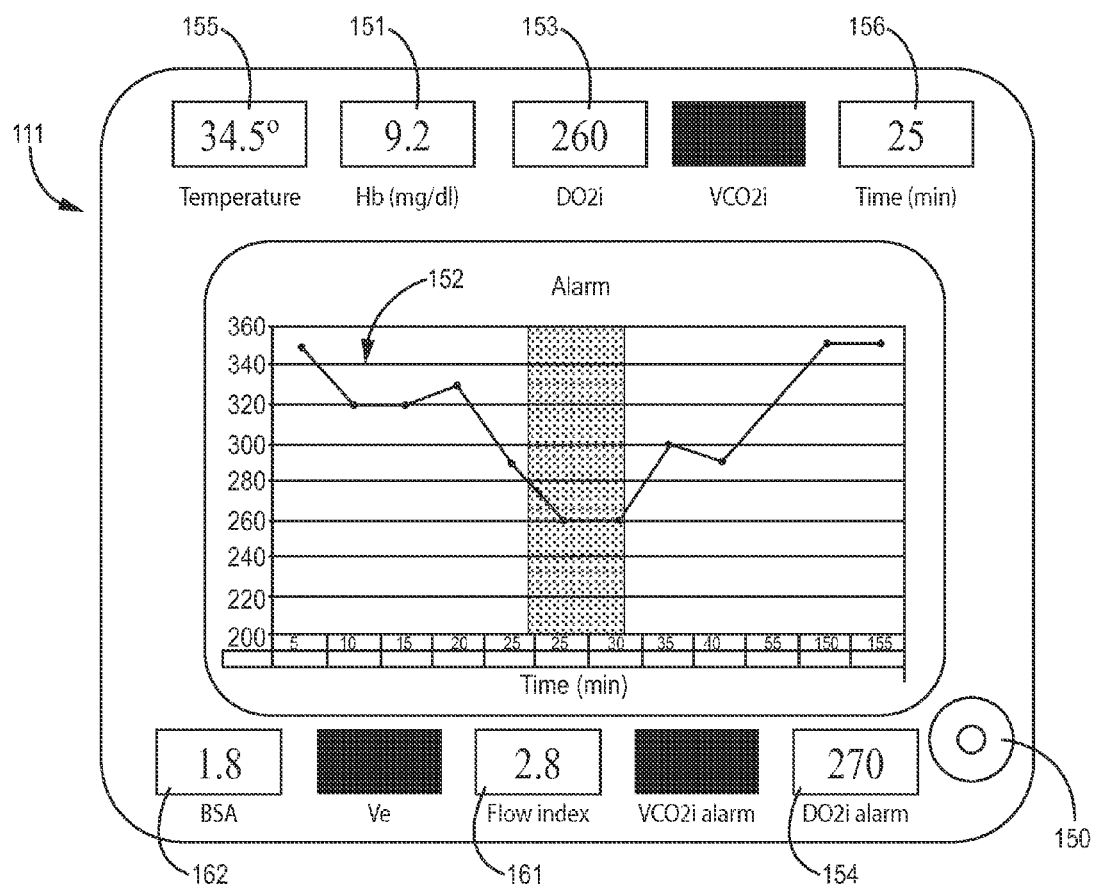
FIG. 21 is a schematic illustration of a screen capture in accordance with an embodiment of the invention.

In some embodiments, the monitoring system 110 may be equipped with a data recording system and a printer interface, and/or a digital data recording system. The display 111 could include two configurations: a complete configuration, as the one shown in FIG. 20, and a reduced configuration, only considering the DO2 parameter, as shown in FIG. 21.

Figure 22:
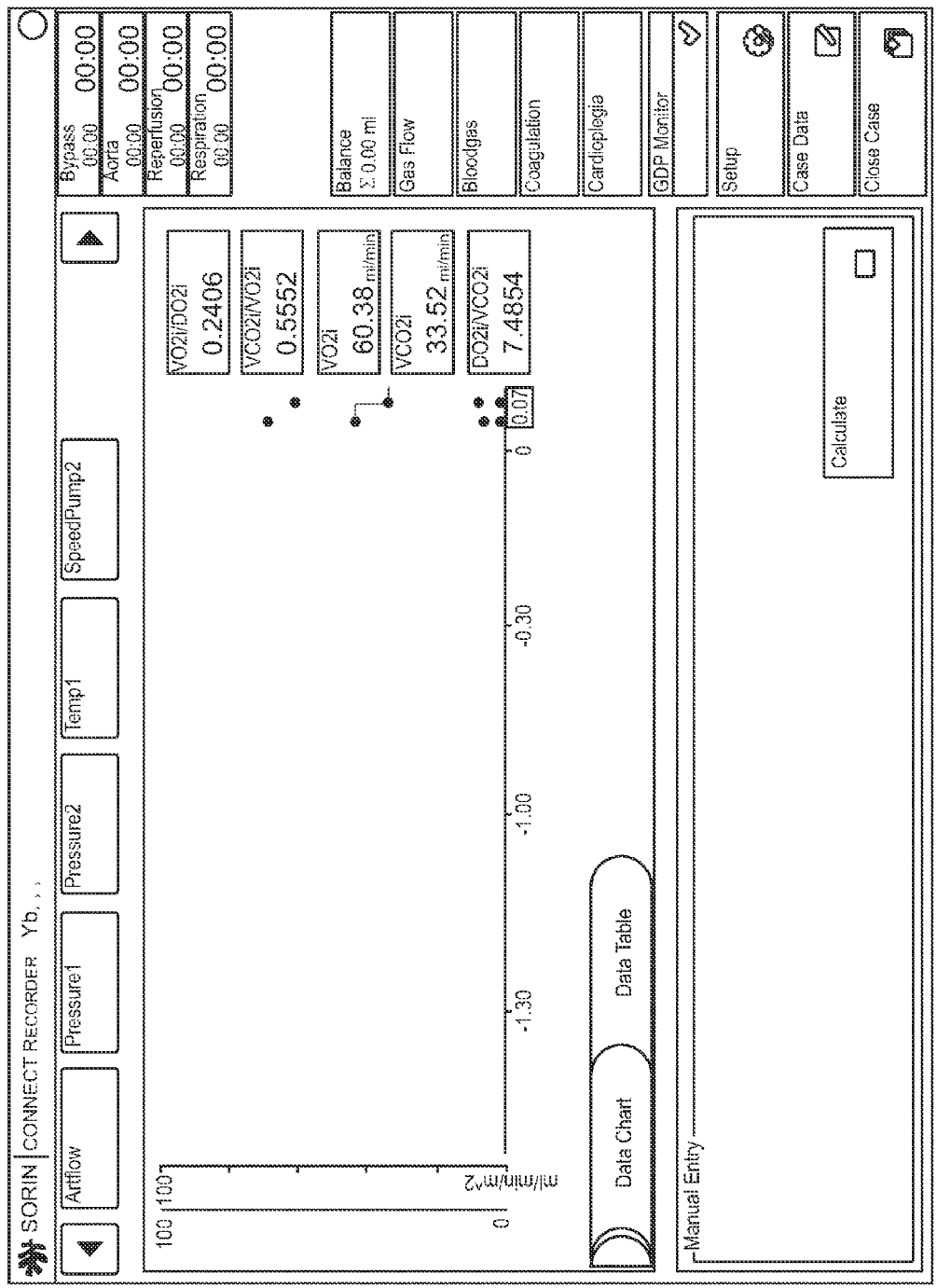
FIG. 22 is a schematic illustration of a screen capture in accordance with an embodiment of the invention.
Figure 23:
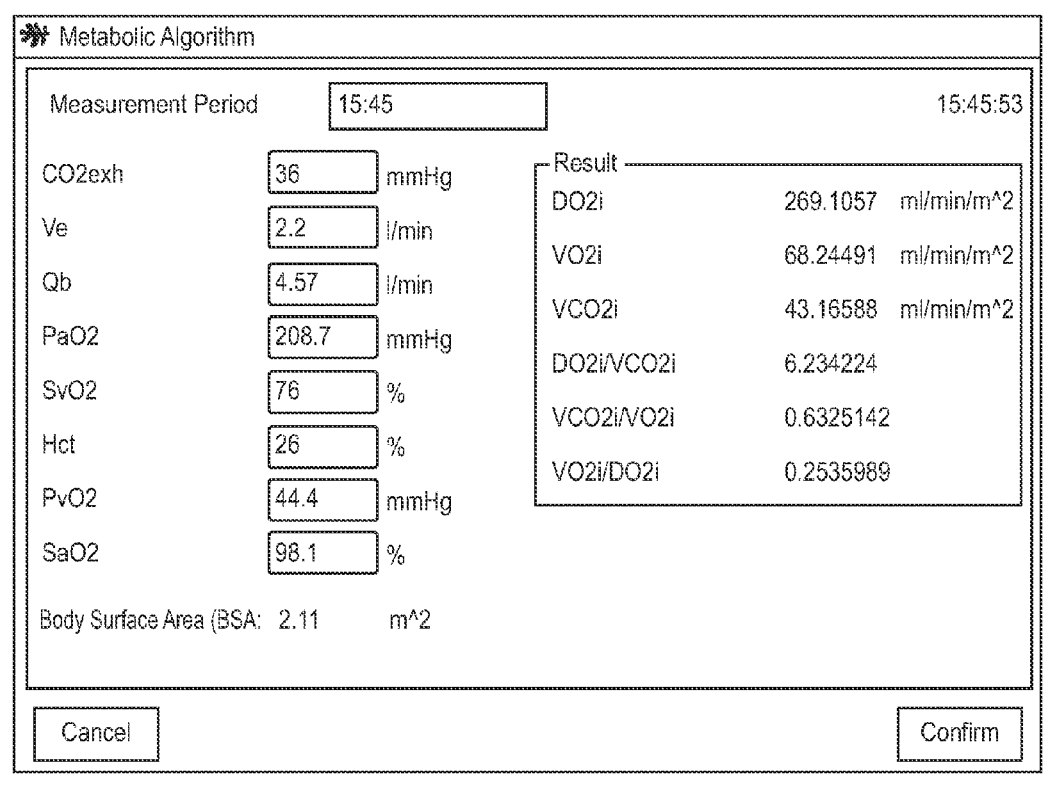

In some embodiments, the DMS 29 may track and display a variety of different metabolic parameters. FIGS. 22 and 23 are screen captures providing illustrative but non-limiting examples of some of the metabolic parameters that can be displayed by the DMS 29. As discussed above, some of these parameters are measured while other parameters may be calculated by the DMS 29 using measured parameters. Examples of parameters include index oxygen delivery (DO2i), indexed oxygen consumption (VO2i), and indexed carbon dioxide production (VCO2i). Examples of ratios that may be displayed include DOi2/VCO2i, VCO2i/VO2i and VO2i/DO2i.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

The invention claimed is:

1. An integrated perfusion system comprising:
   a heart lung machine including
   a plurality of pump modules, each pump module having a control unit;
      a controller in communication with each of the control units;
      an input device in communication with the controller and configured to accept operational settings information from a user; and
      an output device in communication with the controller and configured to display operational parameters of the plurality of pump modules;
   a data management system in communication with the controller, the data management system including:
      an RF sensor; and
      a processor in communication with the RF sensor;
      wherein the data management system is configured to compute and display metabolic parameters; and
   one or more disposable elements comprising at least one oxygenator configured to be used in conjunction with the heart lung machine and each disposable element including an RFID tag programmed with identifying information about the disposable element that can be read by the RF sensor and used by the processor to unlock an algorithm in the data management system if appropriate disposable elements are identified;
   wherein the data management system is configured such that upon receipt of the identifying information from the one or more disposable elements, the processor uses the algorithm and computes and displays the metabolic parameters.

2. The integrated perfusion system of claim 1, wherein the data management system is configured to receive and record data from the heart lung machine and optionally from external sources.

3. The integrated perfusion system of claim 2, wherein the data management system is configured to display data received from the heart lung machine and optionally from external sources.

4. The integrated perfusion system of claim 1, wherein the one or more disposable elements include one or more of a blood reservoir, an oxygenator, a heat exchanger, or an arterial filter.

5. The integrated perfusion system of claim 4, wherein the blood reservoir comprises a venous blood reservoir, a suction blood reservoir, a vent blood reservoir or a combination thereof 6. The integrated perfusion system of claim 1, wherein the one or more disposable elements include a passive RFID tag.

7. The integrated perfusion system of claim 1, wherein the input device comprises a touch screen computer.

8. The integrated perfusion system of claim 1, wherein the RFID tag is further programmed with information identifying performance characteristics of the one or more disposable elements.

9. The integrated perfusion system of claim 8, wherein the data management system is configured to display a priming volume utilizing the identified performance characteristics of the one or more disposable elements.

10. The integrated perfusion system of claim 1, wherein the metabolic parameters include DO2, VO2, VCO2, DO2i, VO2i, and VCO2i.

11. The integrated perfusion system of claim 1, wherein the metabolic parameters include ratios of DO2i/VCO2i, VCO2i/VO2i and VO2i/DO2i.

12. A method of configuring an integrated perfusion system including a heart lung machine and a data management system, the data management system including an RF sensor, wherein the data management system is configured to compute and display metabolic parameters, the method comprising steps of:
   attaching a disposable component comprising an oxygenator and having an RFID tag with identifying information about the disposable component to the heart lung machine;
   reading the RFID tag with the RF sensor;
   unlocking an algorithm within the data management system in accordance with information read from the RFID tag; and
   operating the unlocked algorithm, wherein the data management system is configured such that upon receipt of the identifying information from the RFID tag, the data management system operates the unlocked algorithm and computes and displays the metabolic parameters.

13. The method of claim 12, further comprising displaying information provided from the RFID tag to the RF sensor.

14. The method of claim 12, wherein attaching the disposable component having an RFID tag to the heart lung machine precedes reading the RFID tag with the RF sensor.

15. A method of configuring an integrated perfusion system including a heart lung machine and a data management system, the data management system including an RF sensor and configured to compute and display metabolic parameters, the method comprising steps of:
   attaching a disposable component comprising an oxygenator and having an RFID tag with identifying information about the disposable component to the heart lung machine;
   reading the RFID tag with the RF sensor;
   unlocking an algorithm within the data management system in accordance with the identifying information read from the RFID tag; and
   operating the unlocked algorithm, wherein the data management system is configured such that upon receipt of the identifying information from the RFID tag, the data management system operates the unlocked algorithm and displays a priming volume in accordance with the identifying information read from the RFID tag.

* * * * *